(12) United States Patent
Mueller

(10) Patent No.: US 7,344,537 B1
(45) Date of Patent: Mar. 18, 2008

(54) BONE FIXATION ROD SYSTEM

(75) Inventor: Richard Mueller, Macedonia, OH (US)

(73) Assignee: Theken Spine, LLC, Akron, OH (US)

( * ) Notice: Subject to any disclaimer, the term of this patent is extended or adjusted under 35 U.S.C. 154(b) by 66 days.

(21) Appl. No.: 11/072,987

(22) Filed: Mar. 4, 2005

Related U.S. Application Data

(60) Provisional application No. 60/550,477, filed on Mar. 5, 2004.

(51) Int. Cl.
*A61B 17/70* (2006.01)

(52) U.S. Cl. .................................................... 606/61

(58) Field of Classification Search .............. 606/54, 606/61, 69, 71; 403/342
See application file for complete search history.

(56) References Cited

U.S. PATENT DOCUMENTS

| | | | |
|---|---|---|---|
| 4,653,481 A * | 3/1987 | Howland et al. ............. 606/61 |
| 5,024,213 A | 6/1991 | Asher et al. |
| 5,030,220 A | 7/1991 | Howland |
| 5,074,864 A | 12/1991 | Cozad et al. |
| 5,147,360 A | 9/1992 | Dubousset |
| 5,152,303 A | 10/1992 | Allen |
| 5,261,911 A | 11/1993 | Carl |
| 5,312,405 A | 5/1994 | Korotko et al. |
| 5,330,473 A | 7/1994 | Howland |
| 5,387,212 A | 2/1995 | Yuan et al. |
| 5,470,333 A | 11/1995 | Ray |
| 5,474,555 A | 12/1995 | Puno et al. |
| 5,498,263 A | 3/1996 | DiNello et al. |
| 5,545,167 A | 8/1996 | Lin |
| 5,582,612 A | 12/1996 | Lin |
| 5,613,968 A | 3/1997 | Lin |
| 5,620,443 A | 4/1997 | Gertzbein et al. |

(Continued)

FOREIGN PATENT DOCUMENTS

EP  1 334 703 A2  8/2003

(Continued)

OTHER PUBLICATIONS

C. Hopf, et al., "CDH: Preliminary report on a new anterior spinal instrumentation," European Spine Journal, 1995, pp. 194-199.

*Primary Examiner*—Eduardo C. Robert
*Assistant Examiner*—Nicholas Woodall
(74) *Attorney, Agent, or Firm*—Robert Eichenberger; Eric Killmeier; Middleton Reutlinger

(57) ABSTRACT

An anterior spinal fixation system comprises a plurality of mounting constructs to hold one or more spinal rods or spinal plate-type braces. Each mounting construct includes a bottom plate and a top plate assembly. The bottom plate is attached to the vertebral body with a plurality of anchors, one or more of which may be polyaxial. In one embodiment, the top plate assembly engages the bottom plate through a quick-connect feature that provides simple and secure locking as well as tactile feedback. When the top plate assembly is engaged with the bottom plate, it compresses the rods or braces against the head of the screws, locking the angle of any polyaxial bone screws. In another embodiment, the top plate assembly threadably engages the bottom plate. For additional strength and rigidity, cross-connectors may be used between each pair of mounting constructs when two or more spinal rods are used.

16 Claims, 34 Drawing Sheets

U.S. PATENT DOCUMENTS

| | | |
|---|---|---|
| 5,681,312 A | 10/1997 | Yuan et al. |
| 5,702,395 A | 12/1997 | Hopf |
| 5,713,900 A | 2/1998 | Benzel et al. |
| 5,728,098 A * | 3/1998 | Sherman et al. ............... 606/61 |
| 5,800,433 A | 9/1998 | Benzel et al. |
| 5,843,082 A | 12/1998 | Yuan et al. |
| 5,925,047 A | 7/1999 | Errico et al. |
| 6,036,693 A | 3/2000 | Yuan et al. |
| 6,132,431 A | 10/2000 | Nilsson et al. |
| 6,136,002 A | 10/2000 | Shih et al. |
| 6,193,720 B1 | 2/2001 | Yuan et al. |
| 6,206,879 B1 | 3/2001 | Marnay et al. |
| 6,214,005 B1 | 4/2001 | Benzel et al. |
| 6,228,085 B1 | 5/2001 | Theken et al. |
| 6,413,259 B1 * | 7/2002 | Lyons et al. ................... 606/69 |
| 6,443,953 B1 * | 9/2002 | Perra et al. .................... 606/61 |
| 6,755,829 B1 * | 6/2004 | Bono et al. .................... 606/61 |
| 2005/0171537 A1 * | 8/2005 | Mazel et al. ................... 606/61 |
| 2006/0079892 A1 * | 4/2006 | Roychowdhury et al. ..... 606/61 |

FOREIGN PATENT DOCUMENTS

| | | |
|---|---|---|
| EP | 1 346 708 A1 | 9/2003 |
| JP | 2003250822 A | 9/2003 |

* cited by examiner

BONE FIXATION ROD SYSTEM

CROSS REFERENCE TO RELATED APPLICATION

This application claims priority to and benefit under 35 USC 119(e) U.S. Provisional Application Ser. No. 60/550,477, filed on Mar. 5, 2004, the entire contents of which are herein incorporated by reference.

BACKGROUND OF THE INVENTION

1. Field of the Invention

The present invention generally relates to the correction of spinal deformities. Specifically, the present invention provides an improved apparatus and method for maintaining vertebrae in a desired spatial relationship.

2. Background

The human spinal column is composed of many vertebral bones stacked one upon the other, with an intervertebral disc between each pair of adjacent vertebral bones. The discs act as cartilaginous cushions and shock absorbers. The spinal cord runs in a bony canal formed by successive openings in these bones. Spinal nerves exit the spinal cord between pairs of vertebrae and supply nerve signals to and from other body structures.

Various problems with the human spine have been encountered that adversely affect its health. These problems include spinal column disorders such as scoliosis, kyphosis, spondylolisthesis, as well as traumatic events such as ruptured or slipped discs, broken or fractured spinal columns, and the like. Various forms of instrumentation and procedures are known for the surgical treatment of spinal disorders, for example, Harrington Spinal Instrumentation, Bobechko Hooks, Edwards Hooks and Rod Sleeves, Luque Segmental Spinal Instrumentation and Luque Rectangles, the Dunn Anterior Spinal System, and the Kostuik-Harrington Instrumentation.

The use of longitudinally extending surgical rods in the treatment of diseases or instability of the spine is well known in the medical arts. Such rods achieve rigid spinal fixation when mechanically coupled to bone anchors, such as hooks or screws. These surgical rods are used, generally, in pairs placed on the posterior surface of the left and right sides of the lamina of the human spine.

Some of the above systems utilize hook-type members, which are merely hooked over the laminae or on selected transverse processes of the spine. Other systems, such as the Luque Segmental Spinal Rectangles (used to stabilize spinal fractures and low back fusions), use Luque wires to secure the rectangle to the spine. In some of the prior art systems, screws are used to hold a single rod in place. In other systems, screws are used to hold a slotted plate in place, the location of the screws and slots being such that the plate is moved in order to align the plate apertures or slots with the end of the screw, a nut being used to hold the plate to the screw. With this latter arrangement there is little purchase between the plate and the screw and nut since only a small portion of the plate is engaged adjacent to the slots. Also, the plate cannot be configured to a fixed and stable curvature to follow the curvature desired by the surgeon.

Another known corrective device includes a plurality of plates. Each of the plates is secured over one end of a vertebra. Fasteners are connected to the vertebrae through the plates. A cable is then crimped in the head of the fastener to attach the cable to one vertebra. Tension is put on the cable while it is crimped to an adjacent vertebra until the desired correction is accomplished. This device can only put compressive forces on the spine so that the cables are always in tension. Once the cable is crimped in place, no further adjustment between the crimped fastener and cable is possible.

In devices utilizing rods, the corrective forces are generated by (usually) two rods that are wired around the spine. The rods may be bent to a desired curvature. The rods are not directly attached to all the vertebrae that the rods span; rather, they span numerous vertebrae and are connected to only a few vertebrae using anchors, generally hooks or screws.

One widely used anchor for rod systems is the conventional orthopedic hook having a block-shaped head portion with a central, cylindrical bore therethrough, and a hook portion. The bore of the conventional orthopedic hook is adapted to receive the surgical rod, and the head is slidably positioned over the surface of the surgical rod to the selected vertebra for attachment. The hook may have a variety of different shapes, lengths and openings to accommodate the specific vertebra to which it is to be anchored. With the hook portion properly anchored, the conventional orthopedic hook is locked to the surgical rod either by ratchet or by one or more set screws located within the block-shaped head. However, these systems do not provide polyaxial alignments of the anchors. Rather, the anchors are fixed in a given orientation with respect to the bone and allow no movement in vivo or in response to applied loads.

Another type of anchor is a special orthopedic screw having a block-shaped head with cylindrical bore therethrough. The screw, when its threaded end is attached to the selected anatomical site, is adapted for receiving and passing the elongated surgical rod through its cylindrical bore. Since the shank and threaded end of the screw extends perpendicularly with respect to the axis of the bore, once the screw has been anchored, the position of the head, with its cylindrical bore, is fixed with respect to the spine of the patient.

If the nature of the disease of the spine should require the attachment of a number of orthopedic screws at spaced-apart anatomical sites, it will be appreciated that manual insertion of an elongated surgical rod through the bores of the several spaced-apart orthopedic screws is surgically difficult. The alignment of the axis of the bore in the head of each screw must, of necessity, bear some relationship to a common axis related to the axis of the surgical rod, which rod must be inserted through the several bores. Since the nature of the surgical operation places the surgical rod under stress, as by resisting deforming forces of the spine, it will be appreciated that proper positioning of the heads and alignment of the bores of the several anchor attachment members is of paramount concern.

Some systems have attempted to provide bone screw/rod anchor devices that include polyaxial screws, with varying degrees of success. Most systems that attempt to provide for polyaxial capabilities employ a spherical head or ball-shaped head for the screw. While this allows angulation, it also provides an undesirable structure as the spherical head takes up too much space in the construct. Moreover, such systems rely on a locking screw to apply a compressive force between the lower surface of the rod and the upper surface of the ball to "lock" the angle of entry of the screw.

Other devices have used dual rods or an elongated plate-type brace held by a plurality of plates attached to the anterior portion of the vertebral bodies. A common problem with this type of system is the use of spikes extending from the surface of the plates that will be held against the vertebral body. These spikes present a variety of difficulties for the surgeon. First, the surgeon is unable to position the plate against the surface of the vertebra to check how well the plate will sit on the vertebra in the chosen location without driving the spikes into the bone. And, once the spikes are driven into the bone, the plate cannot be repositioned, for example, to relocate a screw hole away from a damaged portion of the vertebral body. Even if it is unnecessary to relocate the entire plate, these spikes also prevent the surgeon from being able to make small adjustments in orientation since the plate is firmly fixed by the spikes penetrating the vertebral body.

Another problem is the use of parts that require precise alignment to properly mate. One example of this is seen in U.S. Pat. No. 6,132,431. This device uses a C-shaped cover that the surgeon must fit over two flanges while holding an elongated plate-type brace in place between the flanges. With this particular device, the surgeon must then hold the brace and the cover in place while threading a set screw through the cover to compress the brace against the mounting plate.

Recognizing that the spinal fixation systems are installed during a surgical procedure while the patient is under anesthesia, it is important that the orthopedic surgeon have available for immediate use a fixation system that has mounting elements that are easily positioned and secured to the vertebrae. The system should also include a means for attaching surgical rods to the mounting elements that quickly and easily secures the rods. In a preferred embodiment, the device should provide the surgeon with a simple, effective lock that also provides the surgeon with tactile feedback that the lock is secure. And all of these features are needed in a low profile, space-efficient device.

BRIEF SUMMARY OF THE INVENTION

The present invention is directed to an anterior fixation system for the spine. The fixation system utilizes a quick connect, or alternatively a threaded mechanism, allowing spinal fixation rods to be quickly and securely connected to plates attached to two or more vertebral bodies without the use of small parts. As an added benefit, if polyaxial screws are used to attach the plates to the vertebral bodies, the system utilizes the compressive force locking the spinal fixation rods in place to lock in the angle of the screws relative to the plates.

The system comprises at least two mounting constructs, each attached to a different vertebral body. Each construct further comprises a bottom plate and a top cap assembly that engage to hold a pair of fixation rods or a plate-type brace in place. Each bottom plate is generally contoured to the anterior surface of a vertebral body and is attached with a plurality of bone screws. The top plate assembly can attach to the bottom plate with an integral quick-connect and quick-disconnect feature.

In a first embodiment of this invention, at least one polyaxial bone screw is used in attaching each bone plate to the vertebral body. This use of polyaxial bone screws and the absence of spikes on the back of the bottom plate provides flexibility to the surgeon in positioning the device in two ways. First, the surgeon can make subtle adjustments by rotating the device about the first screw. It also provides flexibility by allowing the screw to be driven at an angle in which it will seat in solid bone, even if the actual hole location is directly above a damaged spot in the bone.

In one embodiment, a cam lock provides a quick-connect feature of the device. Preferably, the bottom plate has a cam projection with two cam surfaces. The top plate assembly has a cam cap with mating cam surfaces. To assemble, the surgeon places the top cap assembly over the bottom plate, using the cam projection as a guide. Once the mating surfaces of the bottom plate and top plate assembly are touching, the cam cap is rotated using any of a number of standard driving mechanisms. This system requires the use of no small parts since the cam cap is pre-assembled to the top plate assembly before the surgery commences. Additionally, the surgeon knows that only a small turn, preferably 90 degrees, is required to make a secure and reliable connection. Also in this embodiment, there is no danger of cross threading or overthreading this connection.

In a second embodiment a threaded cap can be used in place of the cam cap to lock the bottom plate to the top plate. This embodiment can employ many of the same features as the first embodiment. In place of the cam projections, threaded projections can be employed. In place of the cam surfaces within the top cap, threads can be employed to engage the threads on the threaded projections.

In other arrangements, cross connectors can be used between mounting constructs to provide additional stability and rigidity to the system. These cross connectors are similar to the mounting constructs except the bottom plate in a cross connector does not have holes for bone screws.

BRIEF DESCRIPTION OF THE DRAWINGS

The teachings of the present invention can be readily understood by considering the following detailed description in conjunction with the accompanying drawings, in which.

DETAILED DESCRIPTION OF THE PREFERRED EMBODIMENT

While the present invention will be described more fully hereinafter with reference to the accompanying drawings in which particular embodiments and methods are shown, it is to be understood from the outset that persons of ordinary skill in the art may modify the invention herein described while achieving the functions and results of this invention. Accordingly, the description that follows is to be understood as illustrative and exemplary of specific embodiments within the broad scope of the present invention and not as limiting the scope of the invention. In the following descriptions, like numbers refer to similar features or like elements throughout.

Figure 1:
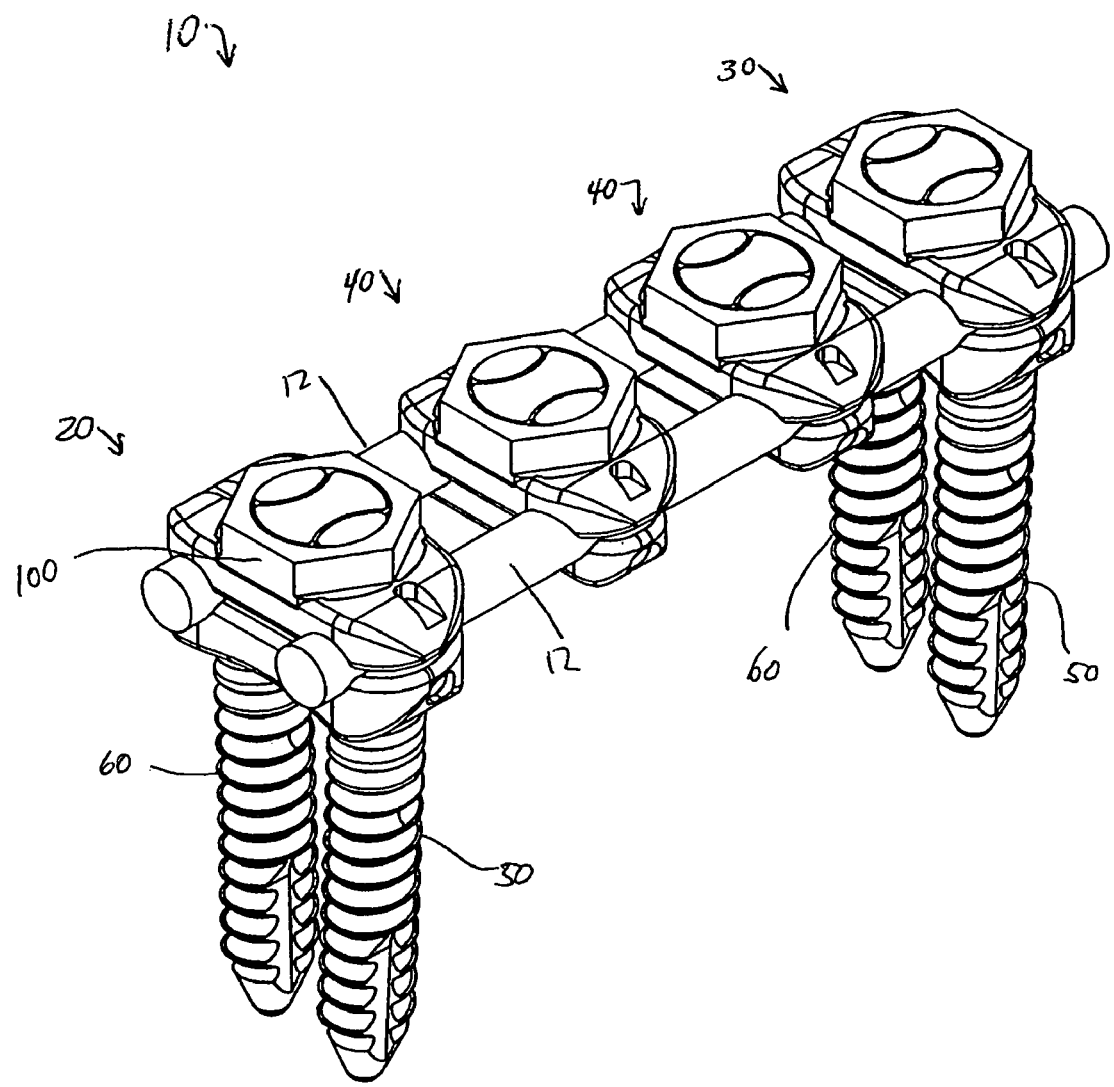
FIG. 1 is a perspective view of a fixation assembly according to an embodiment of the present invention.

Ideally, a spinal fixation system will provide the surgeon with flexibility in attaching the apparatus to the vertebral bodies and a rapid and secure connection to the fixation rods that is safe and secure. The figures depict merely two of many embodiments of the invention: a cam embodiment (FIGS. 1-19) and a threaded embodiment (FIGS. 20-34). FIG. 1 shows an apparatus 10 according to a first embodiment of the present invention. The apparatus 10 generally comprises two or more mounting constructs 20, 30; one or more cross connectors 40, if necessary for added rigidity; two rods 12; two taper lock screws 50; and two polyaxial screws 60. Obviously, however, other configurations are possible.

Figure 2:
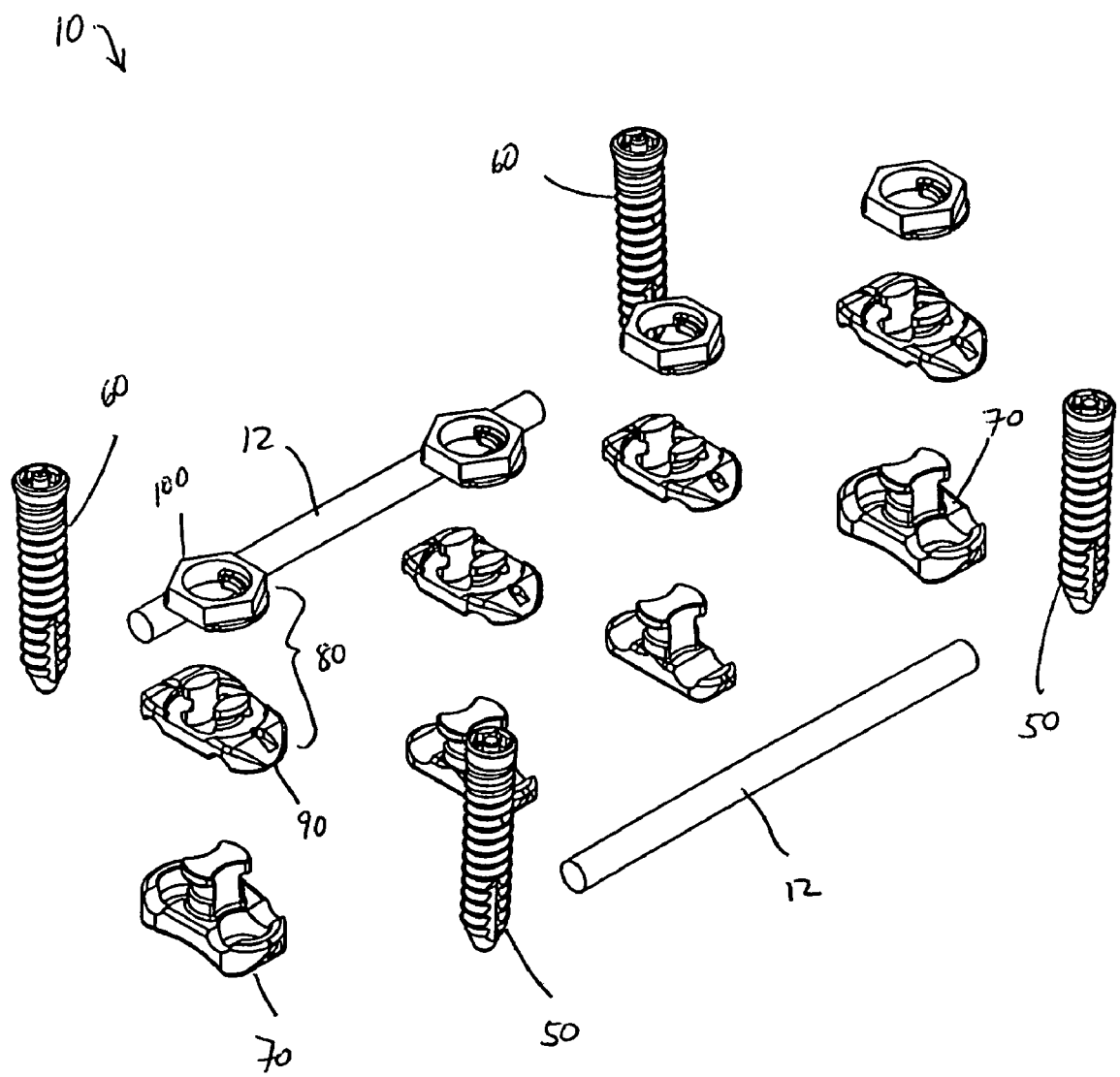
FIG. 2 is an exploded perspective view of a fixation assembly according to an embodiment of the present invention.
Figure 3:
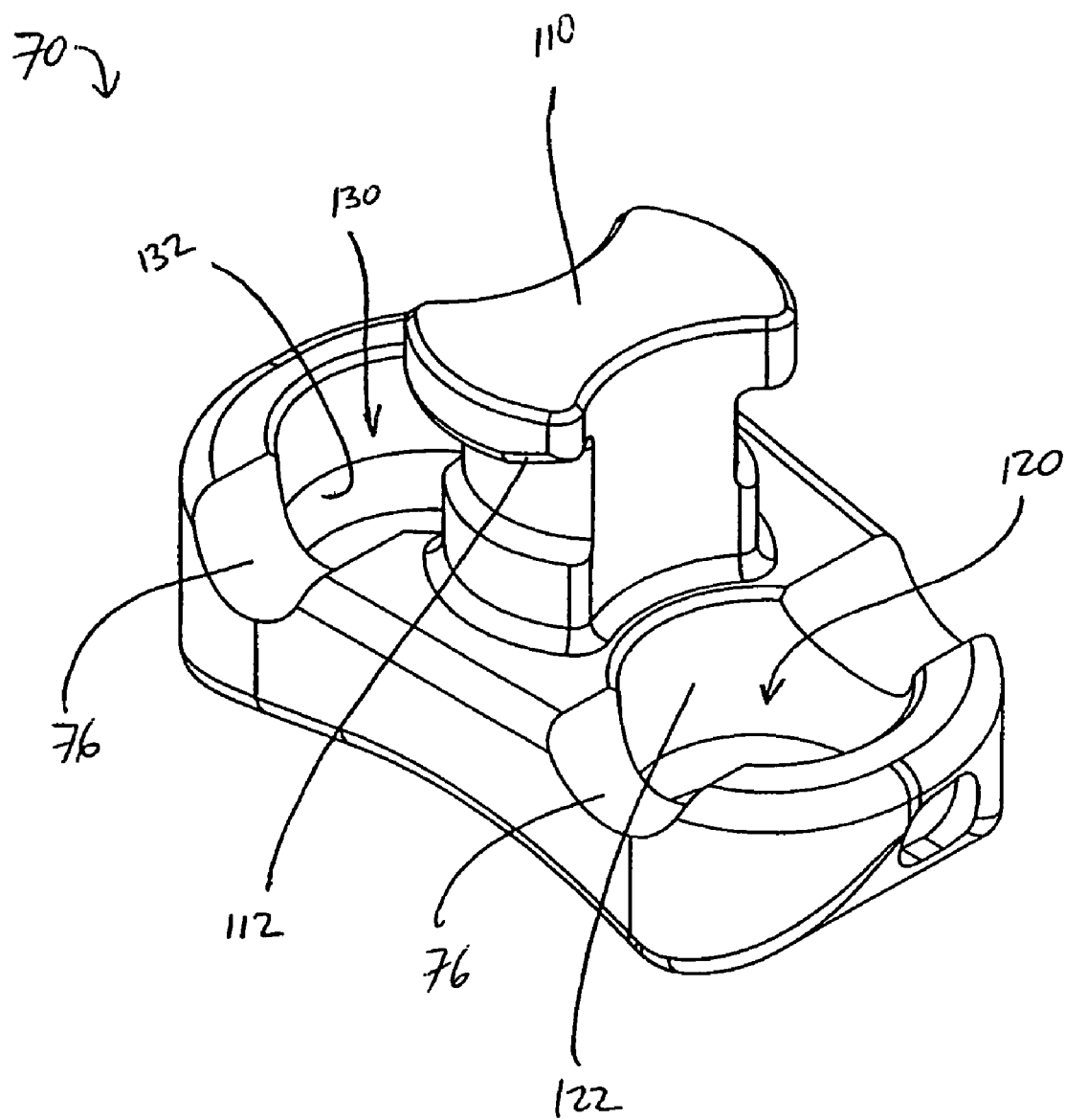
FIG. 3 is a perspective view of a bottom plate according to an embodiment of the present invention.
Figure 4:
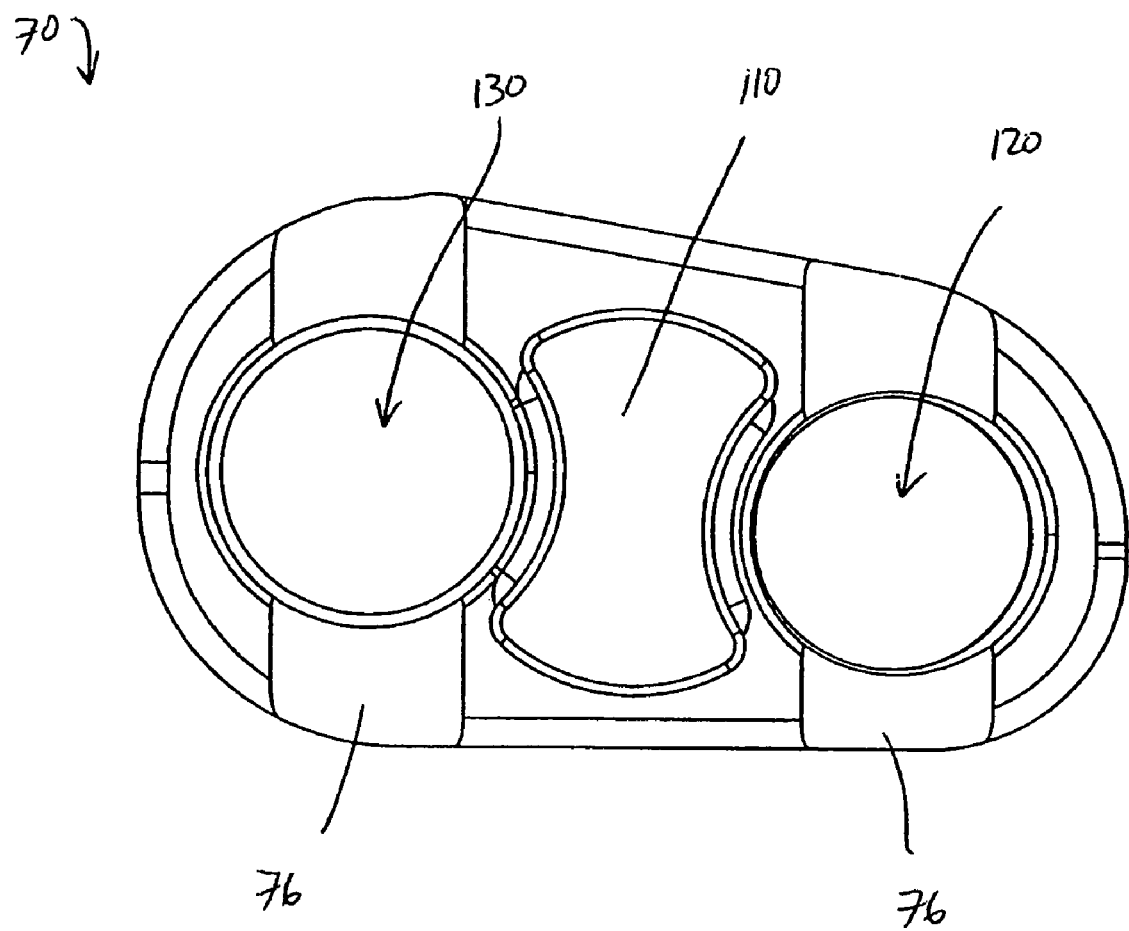
FIG. 4 is a top view of a bottom plate according to an embodiment of the present invention.
Figure 5:
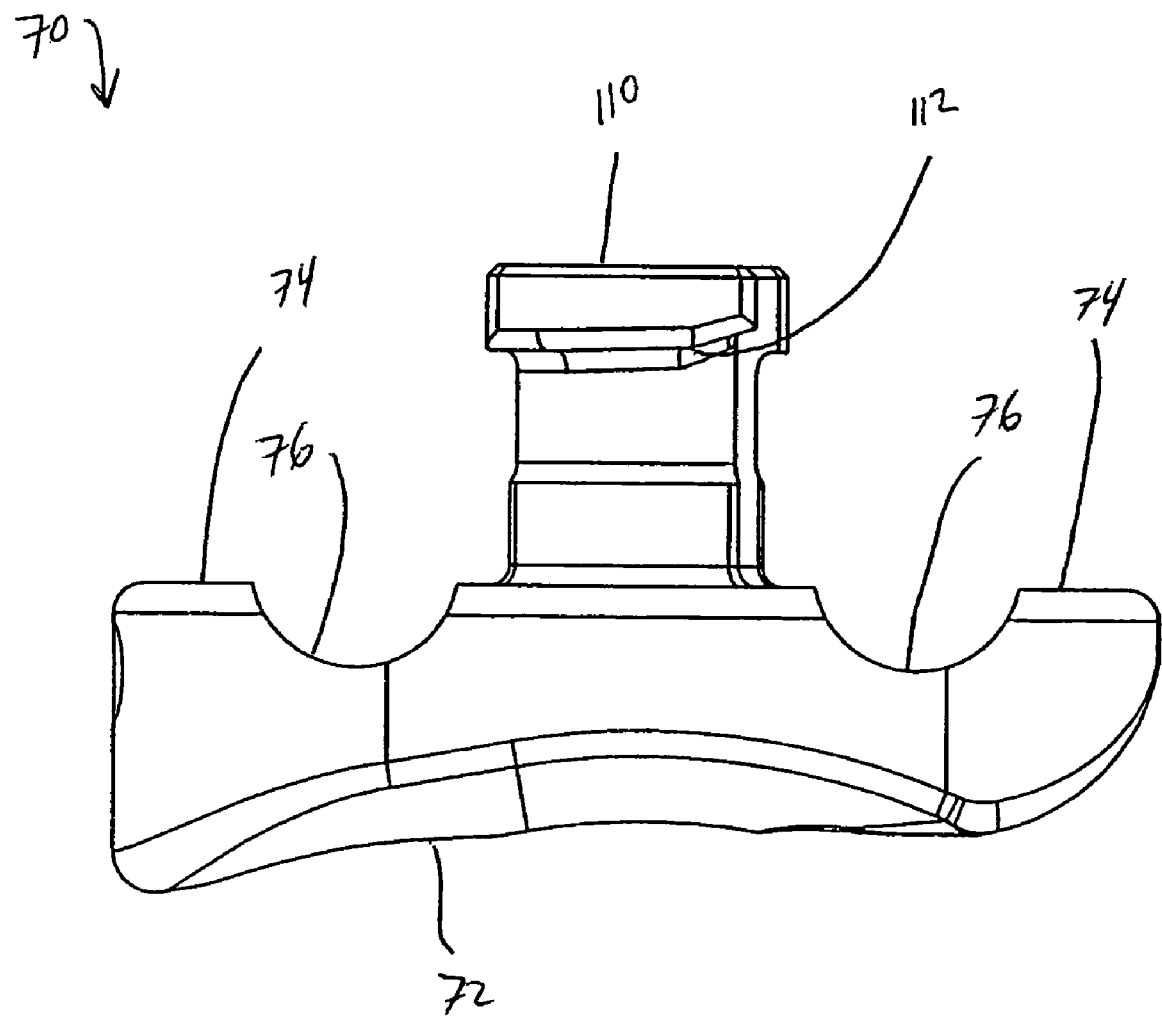
FIG. 5 is a front view of a bottom plate according to an embodiment of the present invention.
Figure 6:
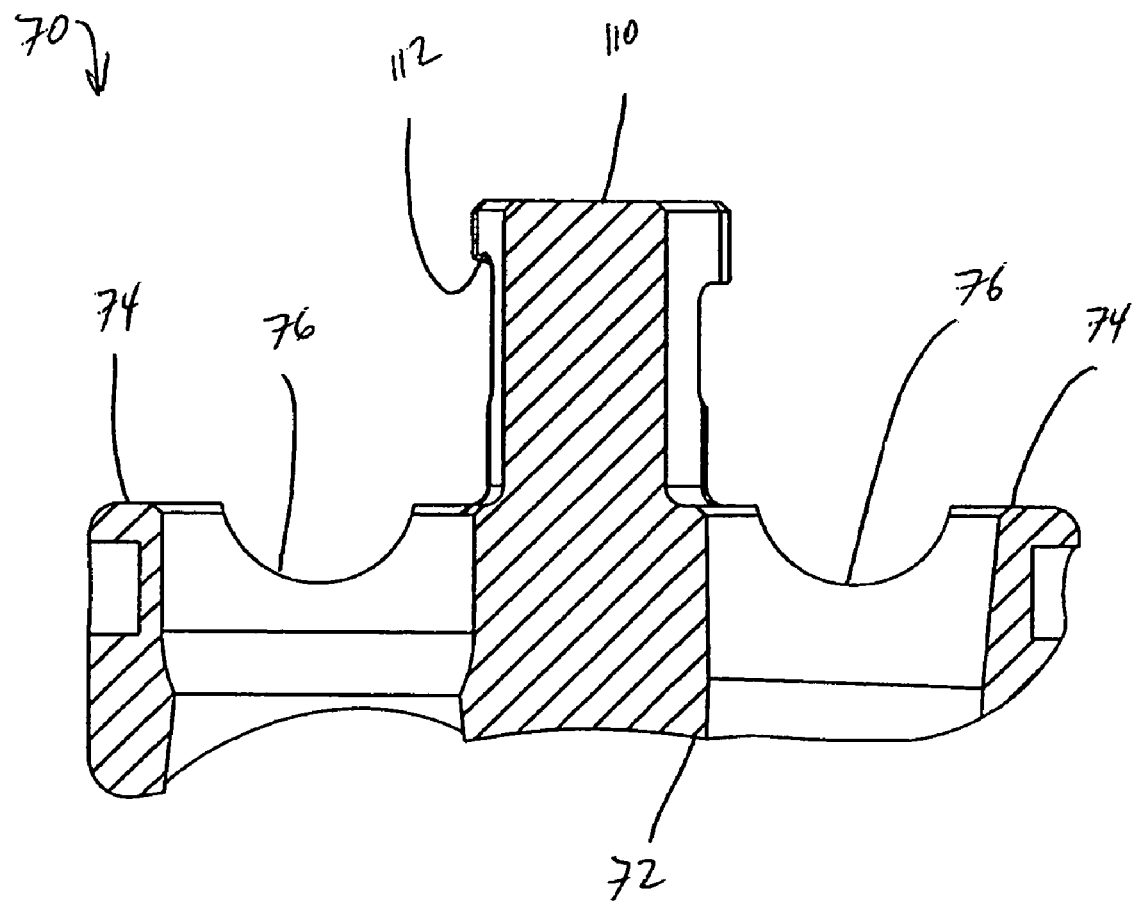
FIG. 6 is a cross-sectional front view of a bottom plate according to an embodiment of the present invention.
Figure 7:
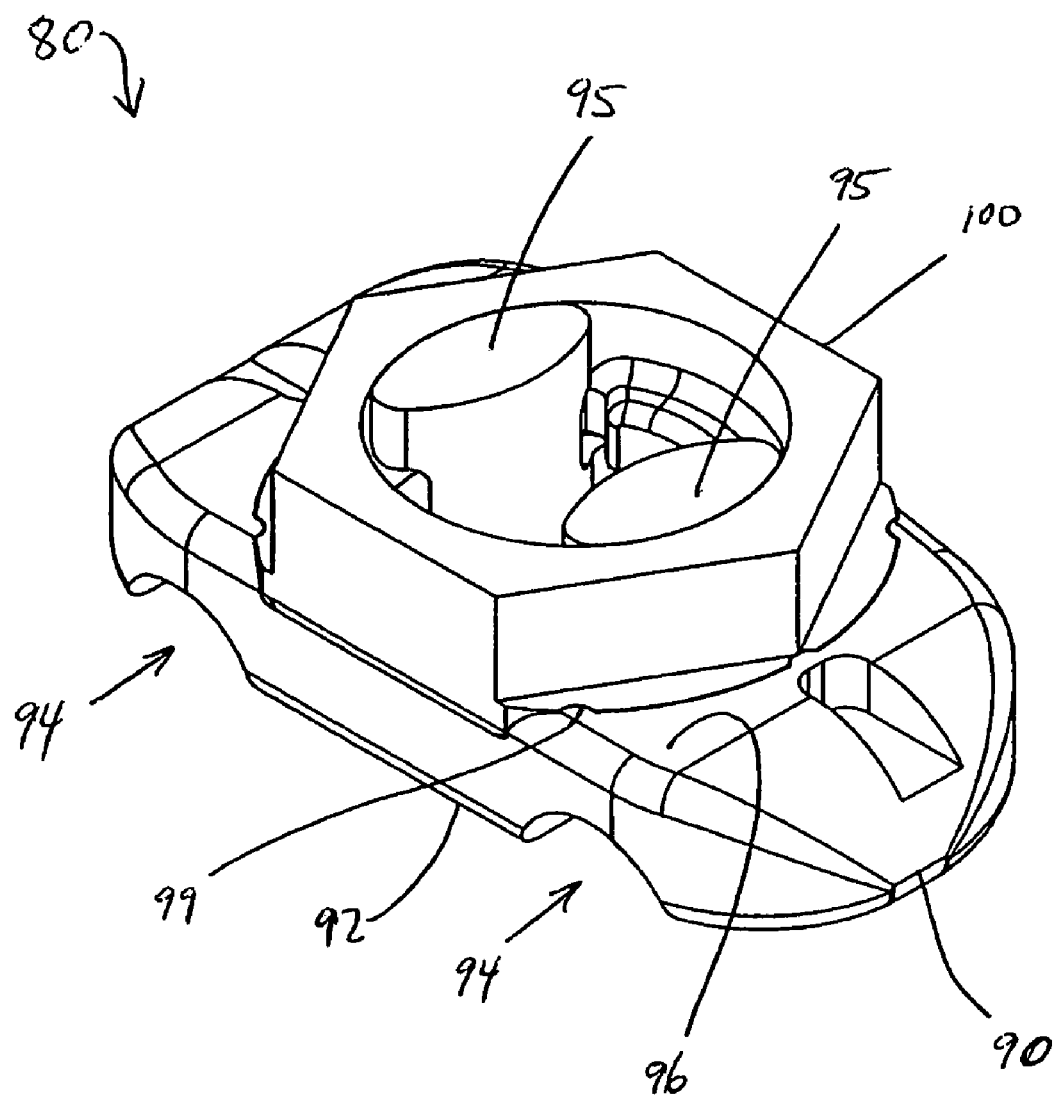
FIG. 7 is a perspective view of a top plate assembly according to an embodiment of the present invention.
Figure 8:
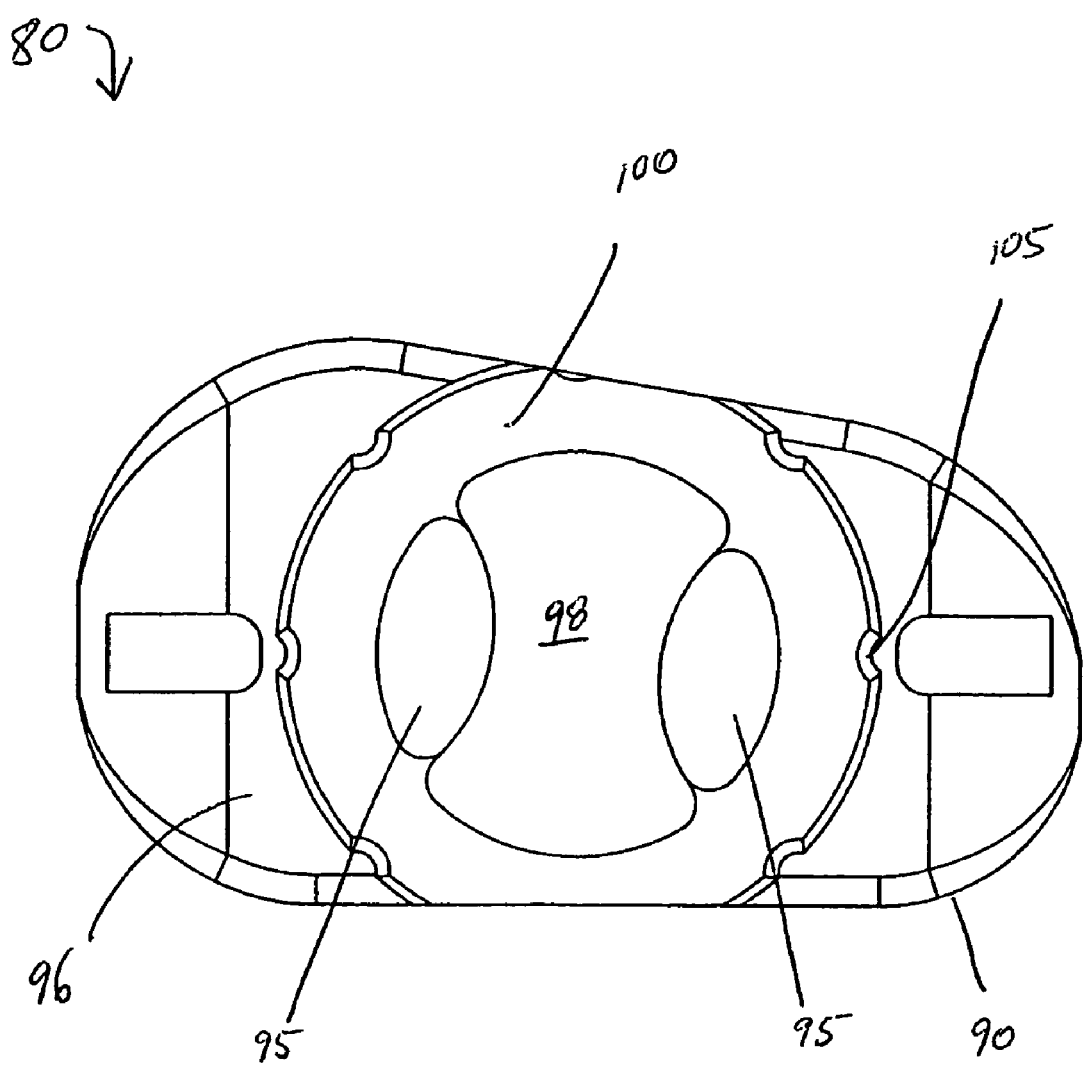
FIG. 8 is a top view of a top plate assembly according to an embodiment of the present invention.
Figure 9:
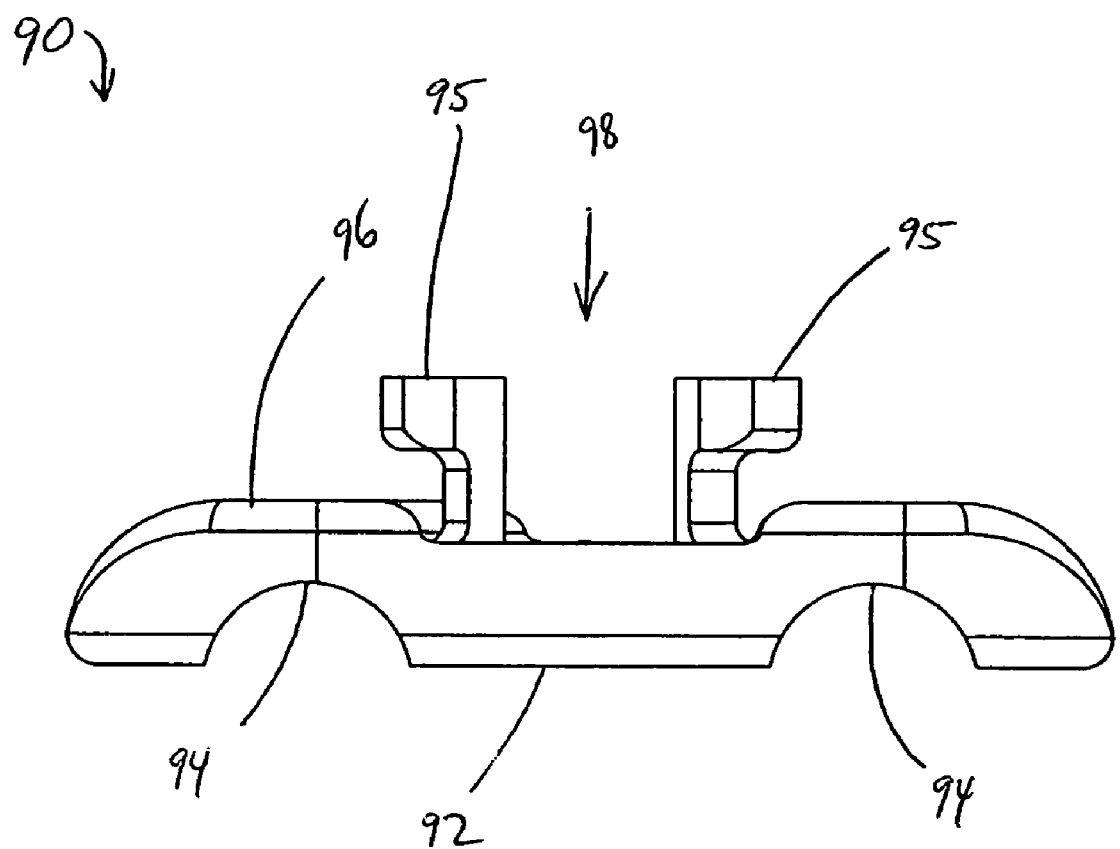
FIG. 9 is a front view of a top plate according to an embodiment of the present invention.
Figure 10:
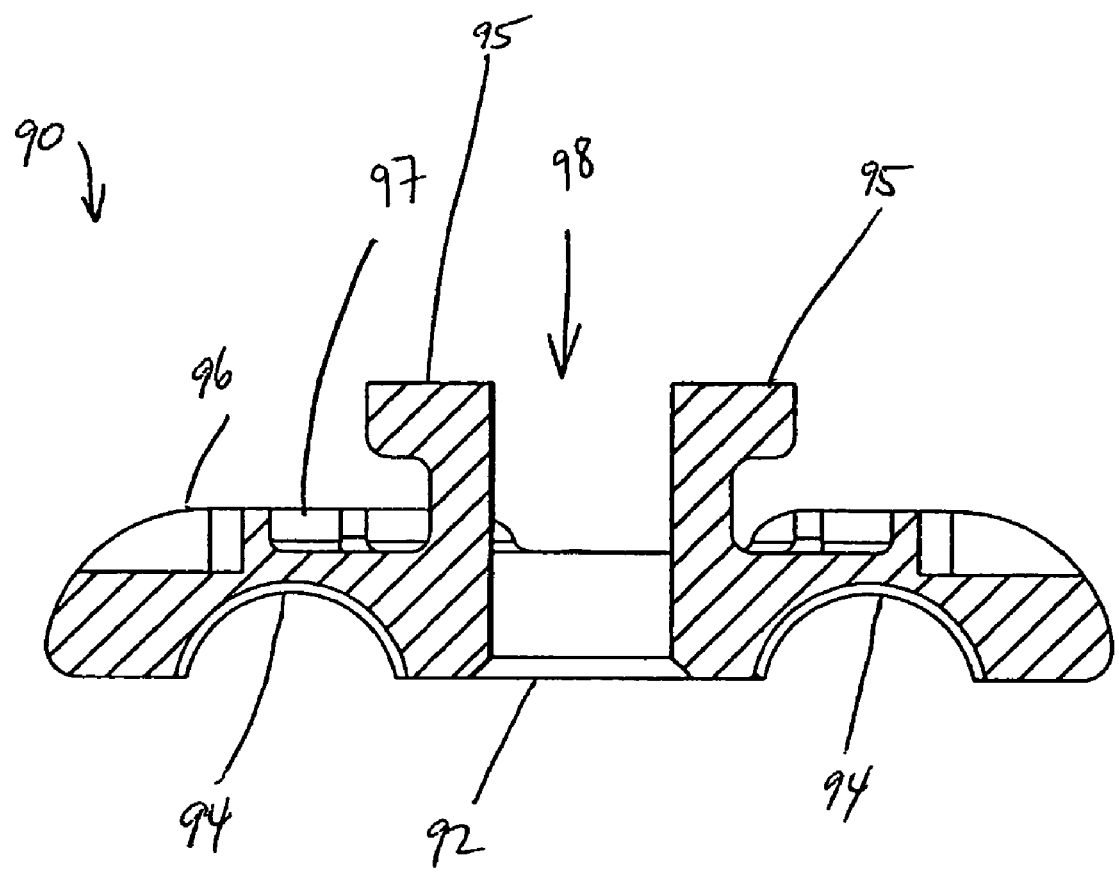
FIG. 10 is a cross-sectional front view of a top plate according to an embodiment of the present invention.

Referring now to FIG. 2, each mounting construct 20, 30 further comprises a bottom plate 70 and a top plate assembly 80, which further comprises a top plate 90 and a cap 100.

Referring now to FIGS. 3-6, the bottom plate 70 has a bottom surface 72 contoured to conform generally to the shape of the vertebral body. Opposite the bottom surface 72, the bottom plate 70 has an upper surface 74 with one or more recesses 76 to accommodate the rods 12.

The bottom plate 70 preferably further contains a first hole 120 and a second hole 130. In the embodiment shown, the first hole 120 has a taper 122 from the upper surface 74 to the bottom surface 72 that acts to lock the angle of the taper lock screw 50 relative to the bottom plate 70. Also in the embodiment shown, the second hole 130 has a spherical undercut 132 to allow the polyaxial screw 60 to be inserted into the bottom plate 70 at varying angles, preferably any angles between 0 and 30 degrees. However, other hole and screw configurations are possible so long as they are designed to allow the screw to seat firmly on the bottom plate. In monoaxial screw embodiments, the top of the head of the screw can be level with or slightly above or below the surface of the recess 76. In polyaxial screw embodiments, the top of the head of the screw is preferably slightly above the surface of the recess 76 so that the rods 12 can lock the angle of the screw upon tightening of the cap 100 and top plate 90.

Referring again to FIGS. 3-6, arising transversely from the upper surface 74 of the bottom plate 70 is a projection 110. The projection 110 can take many forms. Its purpose is to provide a location for a means for coupling or engaging the top plate 90 to the bottom plate 70. The engagement structure of the projection 110 can be viewed as a first engagement structure, while the engagement structure of the cap 100 (described below) may be viewed as a second engagement structure. The cam projection 110 shown in these figures may take many forms in alternate embodiments; it being necessary only to provide a quick lock capability. In the embodiment shown, two cam surfaces 112 are located toward the distal end of the cam projection 110. However, various other arrangements are possible including, but not limited to, arrangements where the cam surfaces are located on the cap 100. The cam surfaces 112 preferably are designed to tightly engage the cap 100 when the bottom plate 70 and the top plate assembly 80 are mated.

Referring now to FIGS. 7-10, the top plate assembly 80, comprising the top plate 90 and the cap 100, is shown. The top plate 90 has a lower surface 92 and an upper surface 96. The lower surface 92 contains two recesses 94 to accommodate the rods 12. The upper surface 96 has a cam cap recess 97. Preferably the top plate 90 further comprises one or more projections 95 that interact with the projection 110 of the bottom plate 70. A hole 98 runs through the cam cap recess 97 allowing the cam projection 110 to pass through the top plate 90 and mate with the cap 100. Preferably, one or more projections 99 can be installed in an inner surface of the cam cap recess 97. These projections 99 can mate with grooves 105 in the cap 100, described below.

Figure 11:
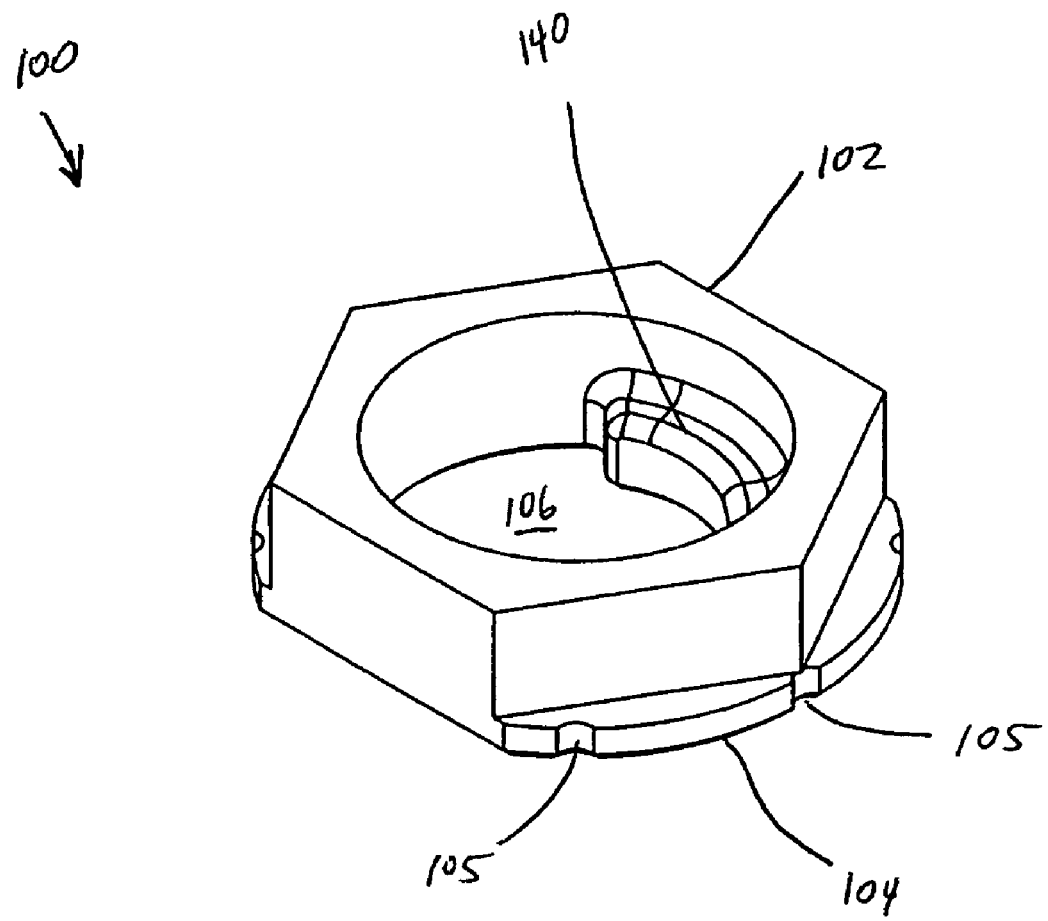
FIG. 11 is a perspective view of a cap according to an embodiment of the present invention.
Figure 12:
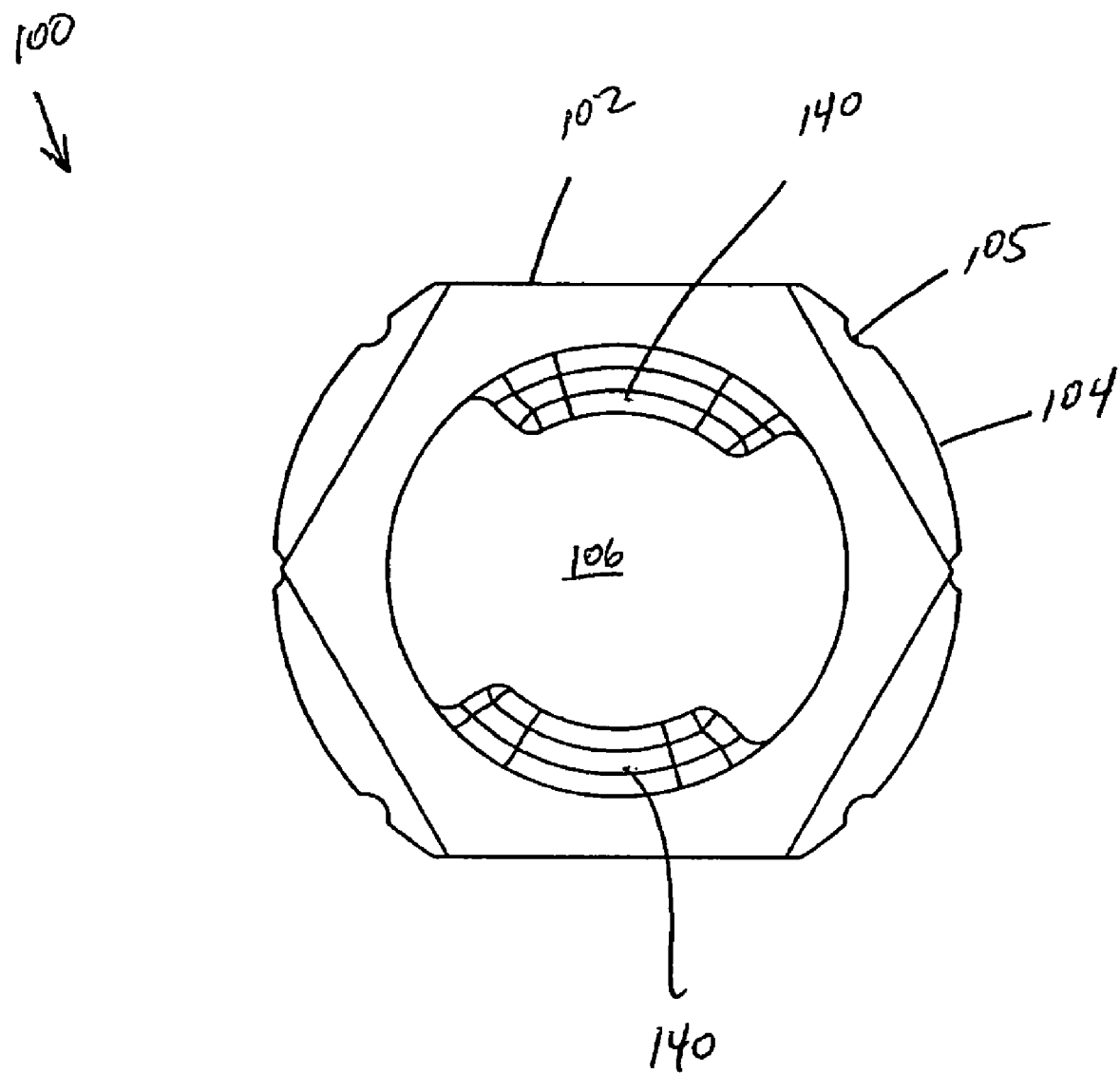
FIG. 12 is a top view of a cap according to an embodiment of the present invention.
Figure 13:
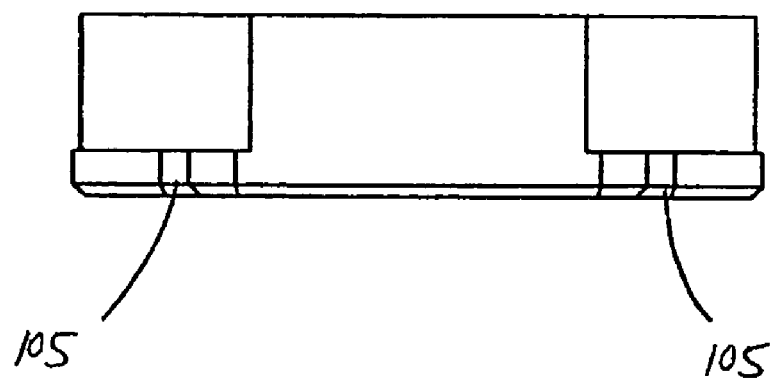
FIG. 13 is a front view of a cap according to an embodiment of the present invention.

Referring now to FIGS. 11-13, the cap 100 preferably has a hexagonal upper portion 102, a lower portion 104, and a centrally located hole 106. The hexagonal upper portion 102 is dimensioned to fit a standard socket to enable the surgeon to rotate the cam cap with a standard, surgical socket wrench. However, it is readily seen that any type of upper portion 102 is possible to engage the many types of driving devices that exist. The lower portion 104 has a surface that preferably is fitted with one or more grooves 105, or alternatively detents. These grooves 105 or detents can be placed at certain locations about the perimeter of the lower portion 104 so as to correspond with certain known reference points of rotation. For example, three grooves 105 can be placed in the perimeter of the lower portion 104 to correspond to an open position, a closed position, and a midway position. Complementary features can be provided in the cam cap recess 97 to engage the grooves 105 or detents so as to provide a tactile feedback to the surgeon.

Figure 14:
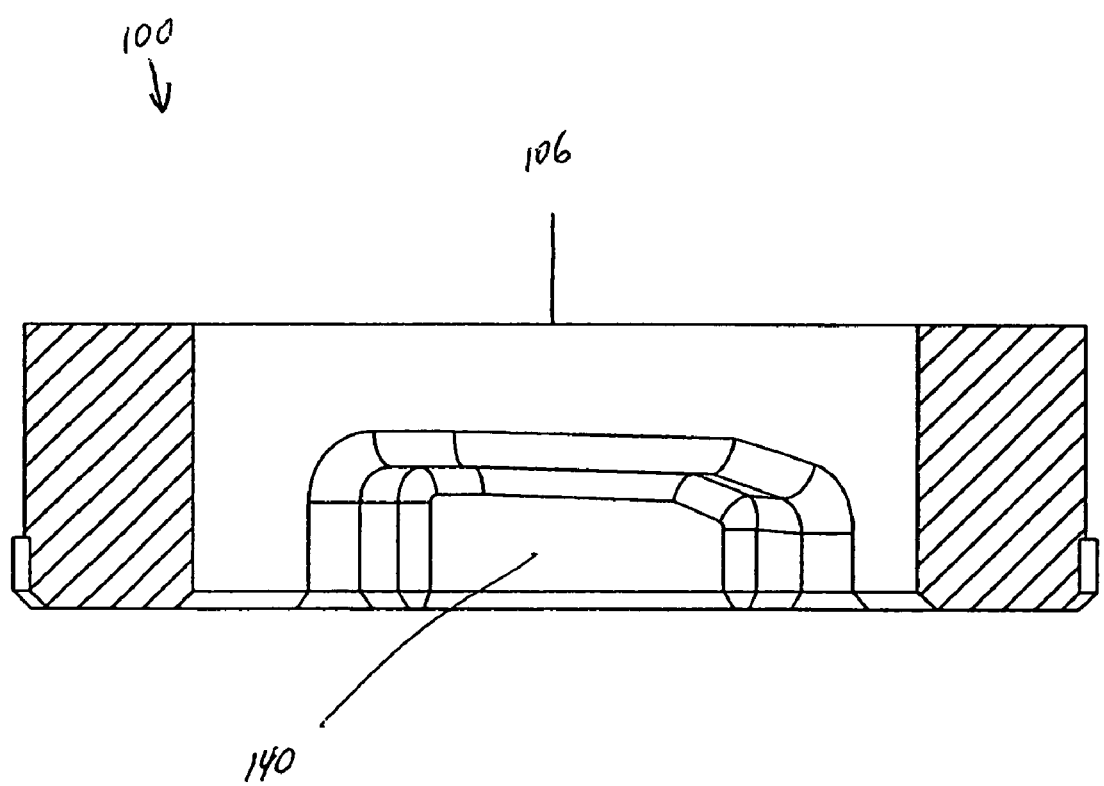
FIG. 14 is a detail view of one of the cam surfaces from the cap shown in FIG. 13.

Referring now to FIG. 14, the hole 106 preferably has two cam surfaces 140 located toward the lower portion of the cap 100 that project inwardly. The hole 106 allows the cam projection 110 to pass through the cap 100 far enough that the cam surfaces 112 of the cam projection 110 of the bottom plate 70 are able to interact with the cam surfaces 140 when the cap 100 is rotated.

Figure 15:
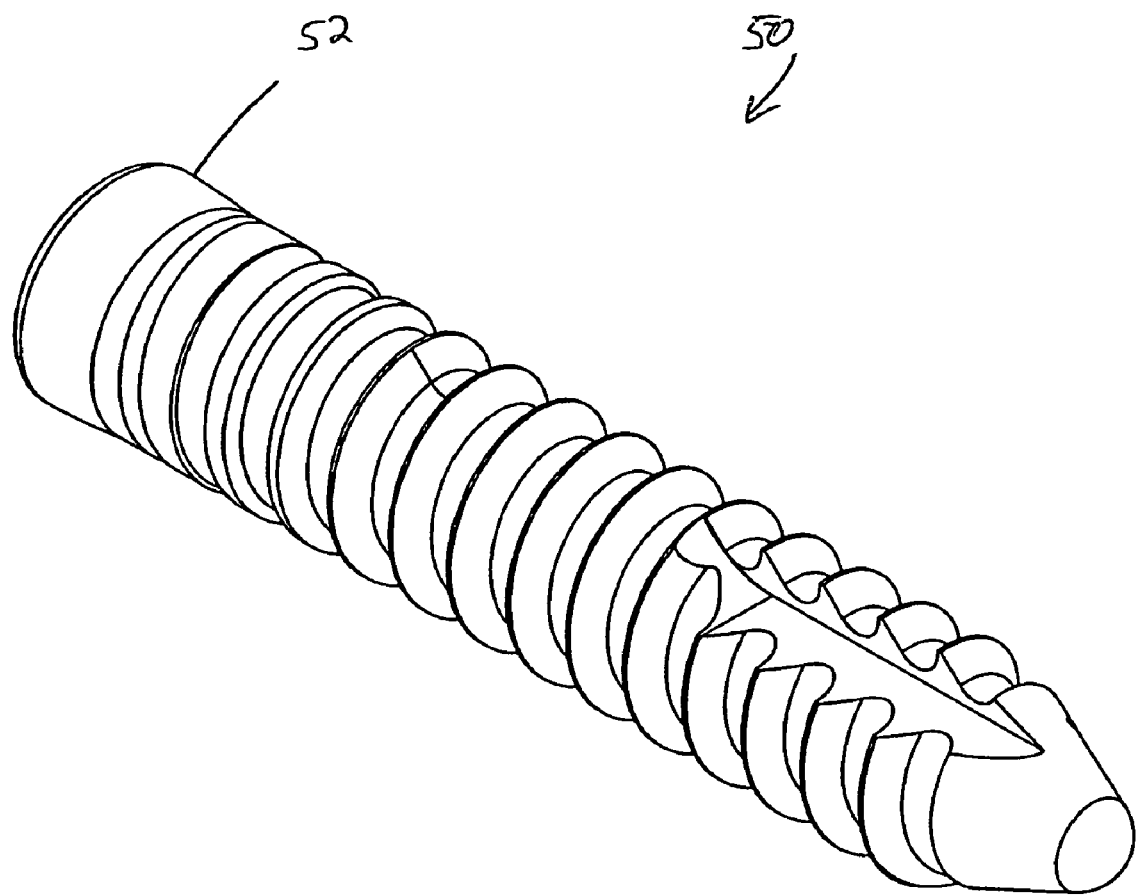
FIG. 15 is a perspective view of a monoaxial screw for use with an embodiment of the present invention.
Figure 16:
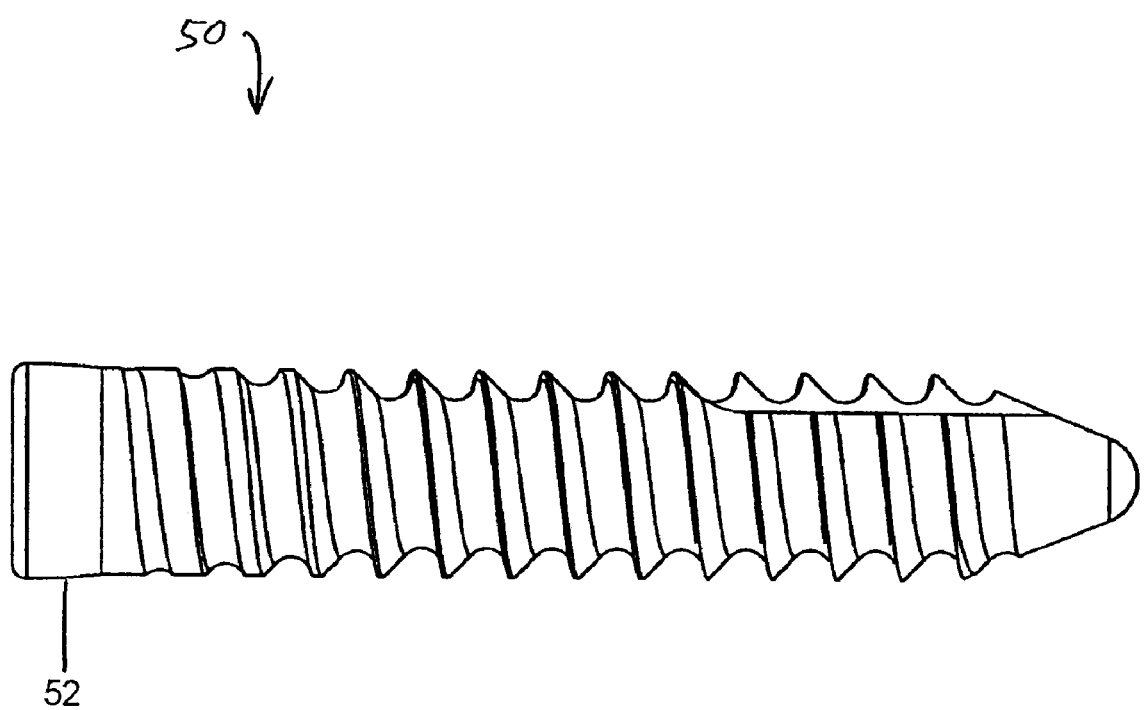
FIG. 16 is a side view of the monoaxial screw shown in FIG. 15 according to an embodiment of the present invention.

Referring now to FIGS. 15 and 16, an exemplary taper lock screw 50 is shown. It should be noted, however, that the invention is usable with various types of fasteners and the description herein of only two exemplary embodiments is not intended to limit the invention in any way. The taper lock screw 50 has a head 52 that is shown (FIG. 19) having a hexagonal recess 54, allowing it to be driven with a standard allen type wrench. It should be noted that many types of driving mechanisms, and therefore recesses 54, are possible. The head 52 is tapered such that, when it is driven through the first hole 120 in the bottom plate 70 and into the vertebral body, it mates with the taper 122 to lock in the angle of the screw relative to the bone plate. Further, after the taper lock screw 50 is driven into the bone, the top surface of the head 52 will be level with the lowest point in the recess 76 such that the rod 12 compresses the head 52 when the cap 100 is rotated to engage the cam projection 110. This relation is shown in detail in FIG. 19.

Figure 17:
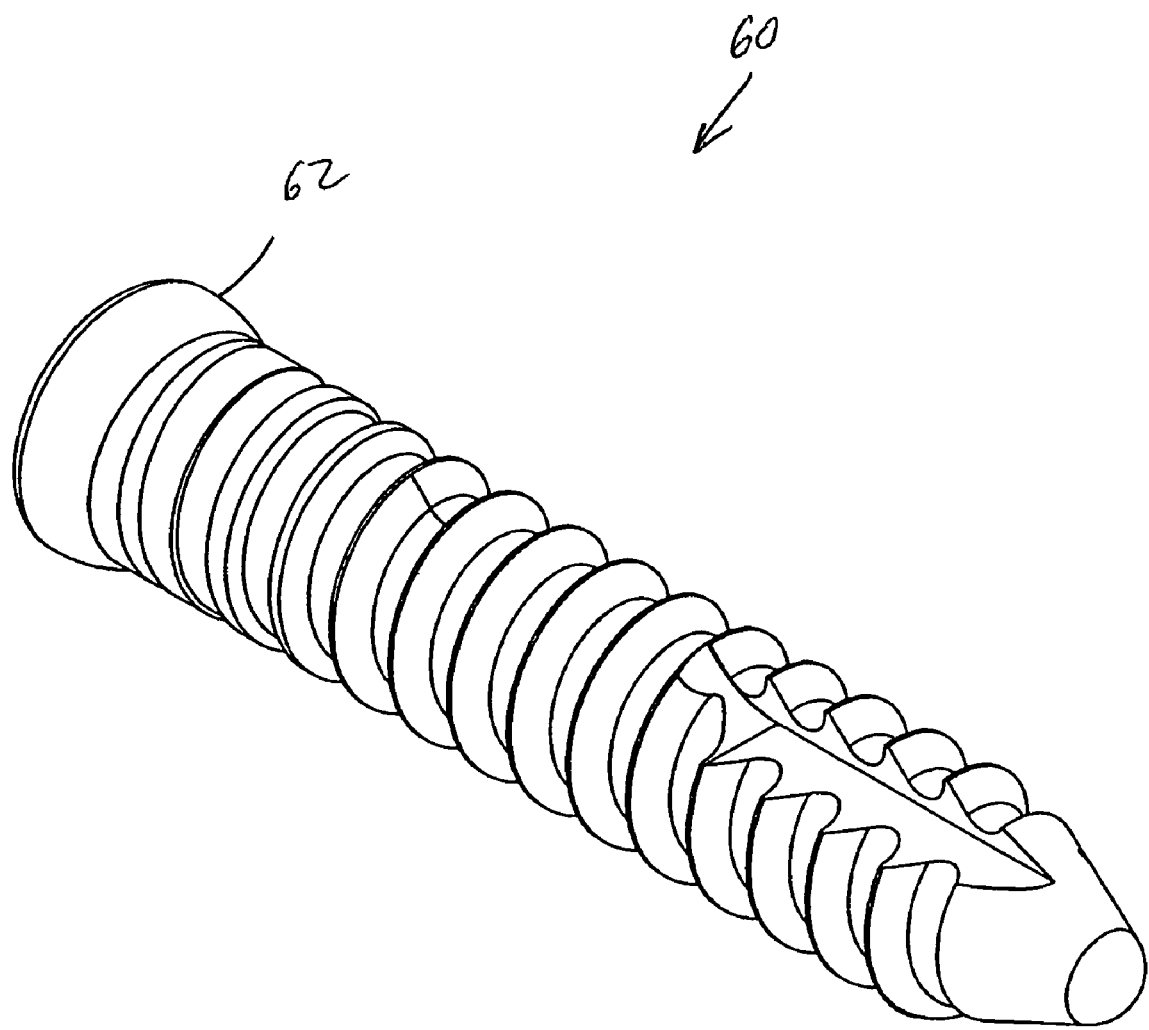
FIG. 17 is a perspective view of a polyaxial screw according to an embodiment of the present invention.
Figure 18:
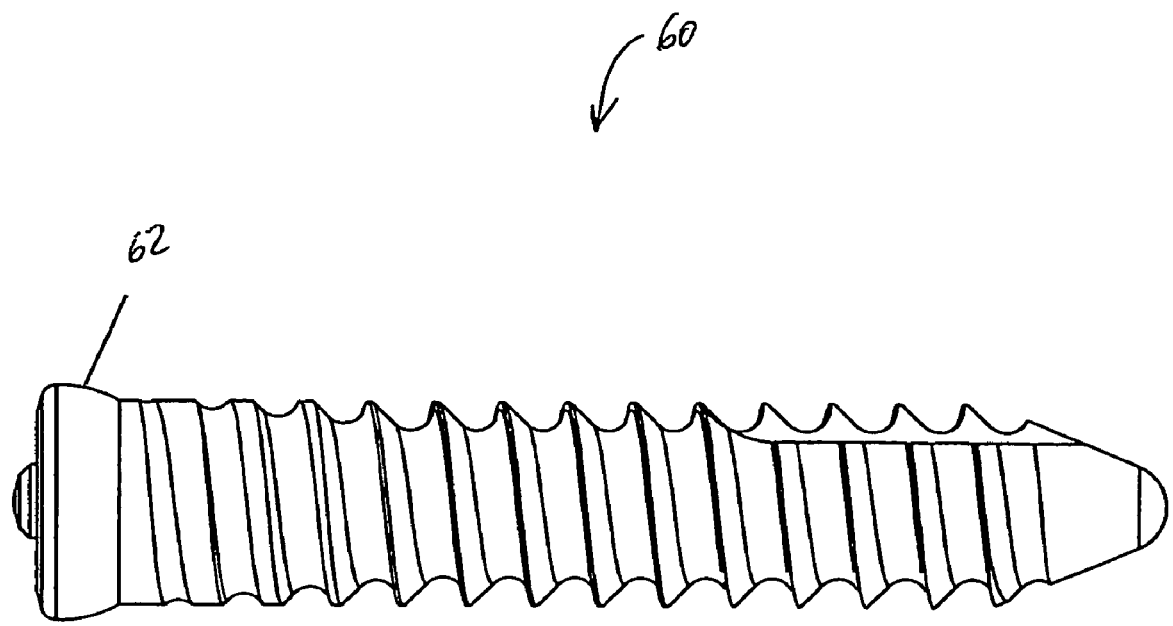
FIG. 18 is a side view of the polyaxial screw shown in FIG. 17 according to an embodiment of the present invention.
Figure 19:
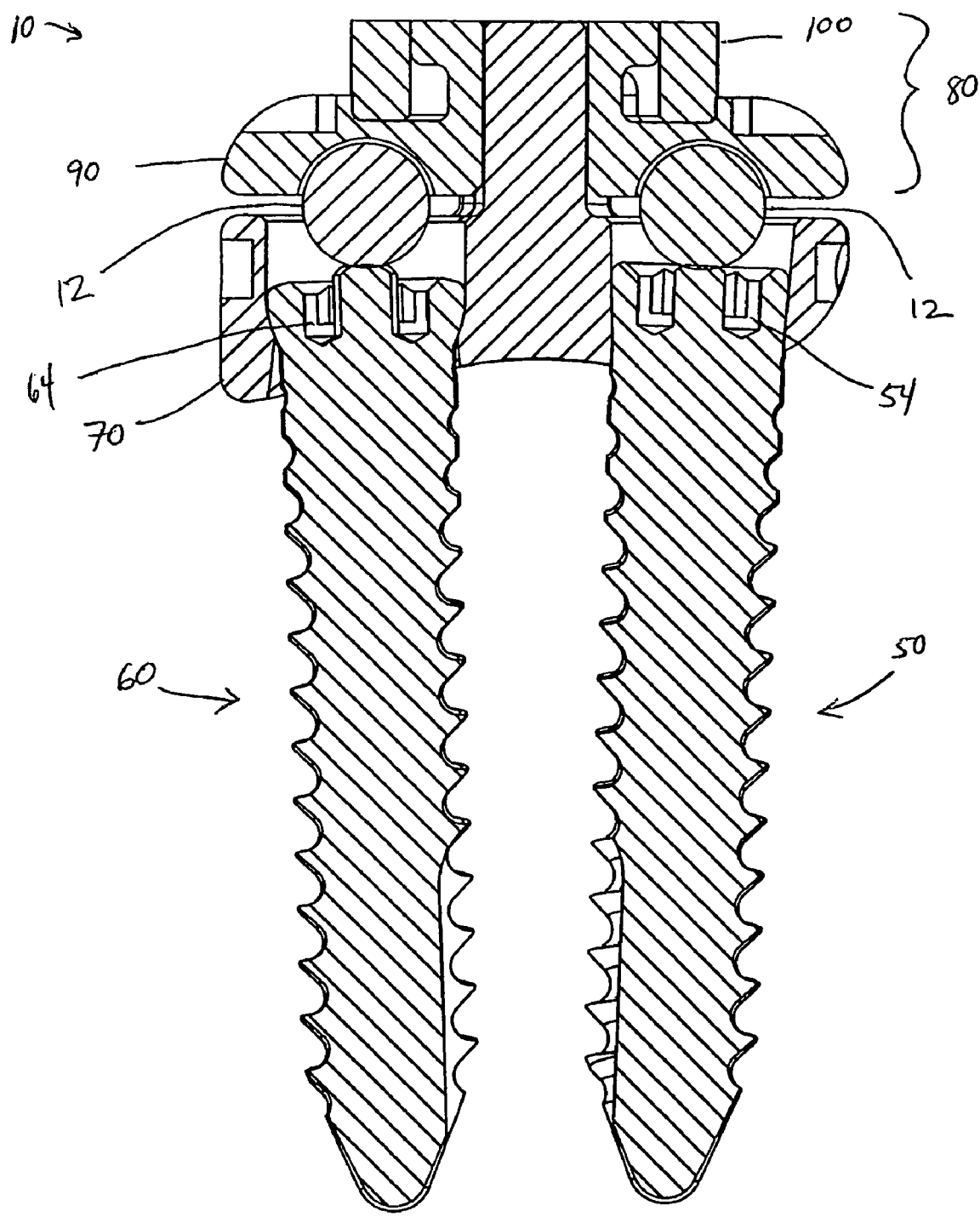
FIG. 19 is a cross-sectional front view of an embodiment of the present invention shown with one monoaxial screw and one polyaxial screw in use.
Figure 20:
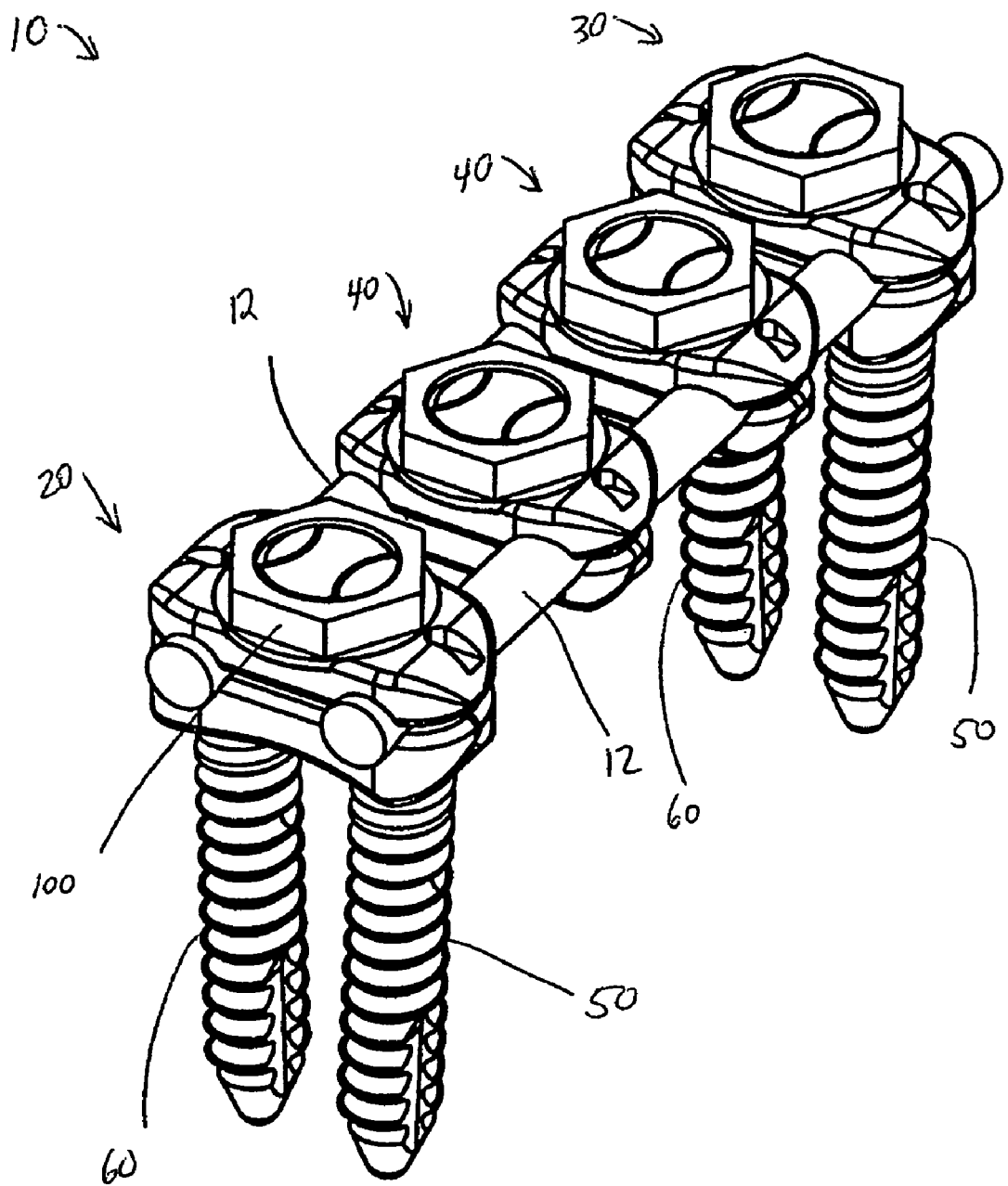
FIG. 20 is a perspective view of a fixation assembly according to a second embodiment of the present invention.
Figure 21:
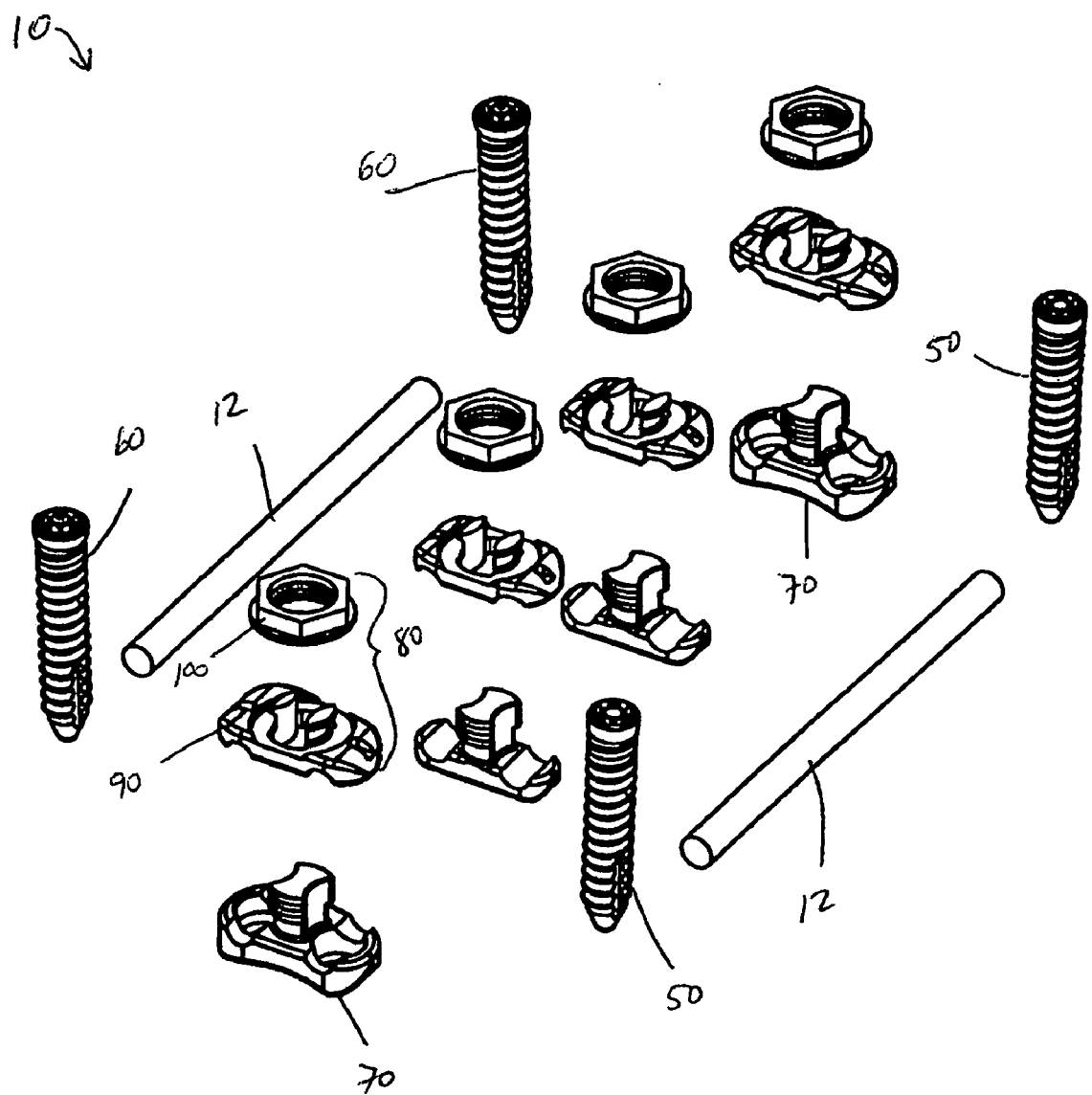
FIG. 21 is an exploded perspective view of a fixation assembly according to a second embodiment of the present invention.
Figure 22:
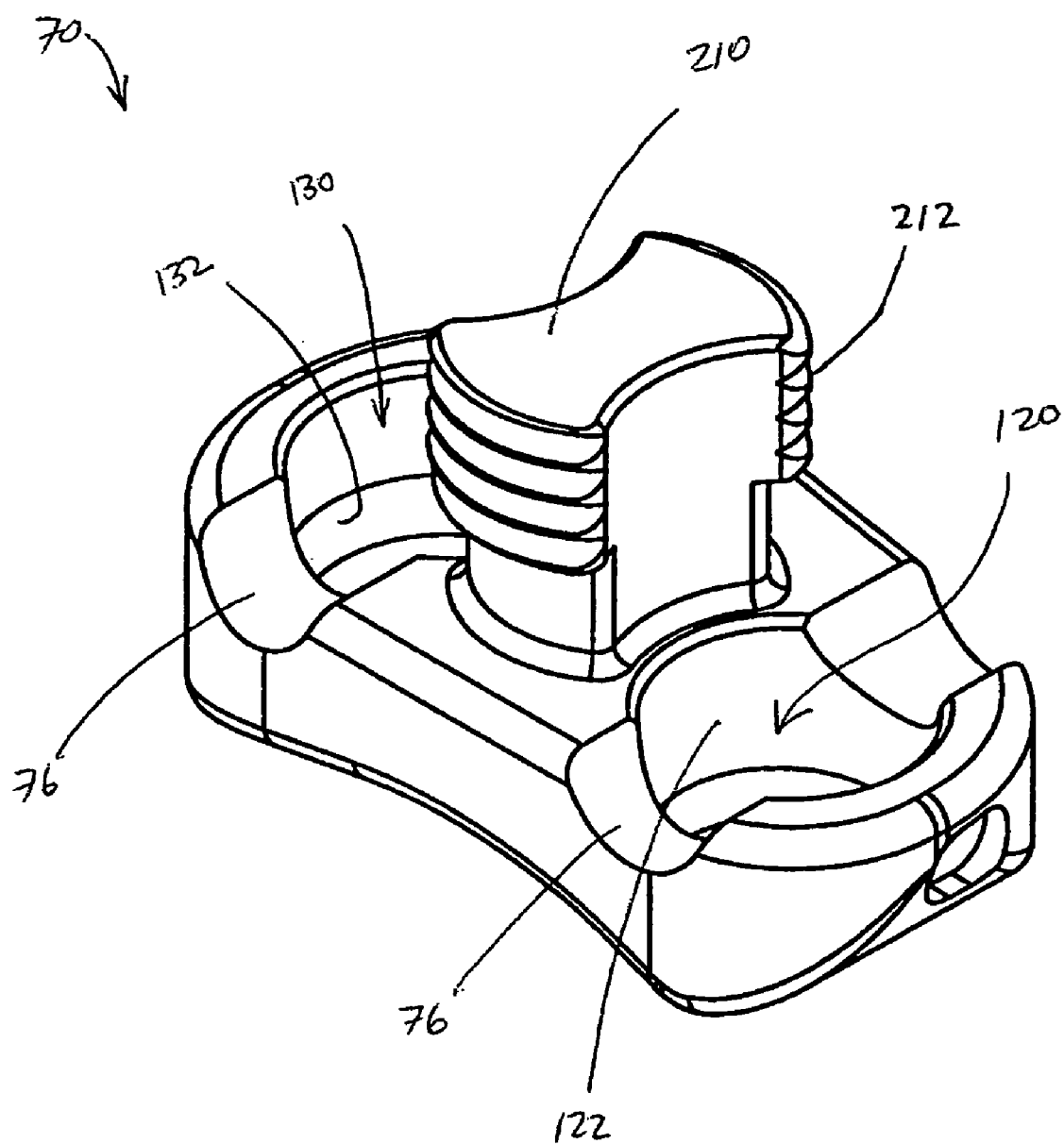
FIG. 22 is a perspective view of a bottom plate according to a second embodiment of the present invention.
Figure 23:
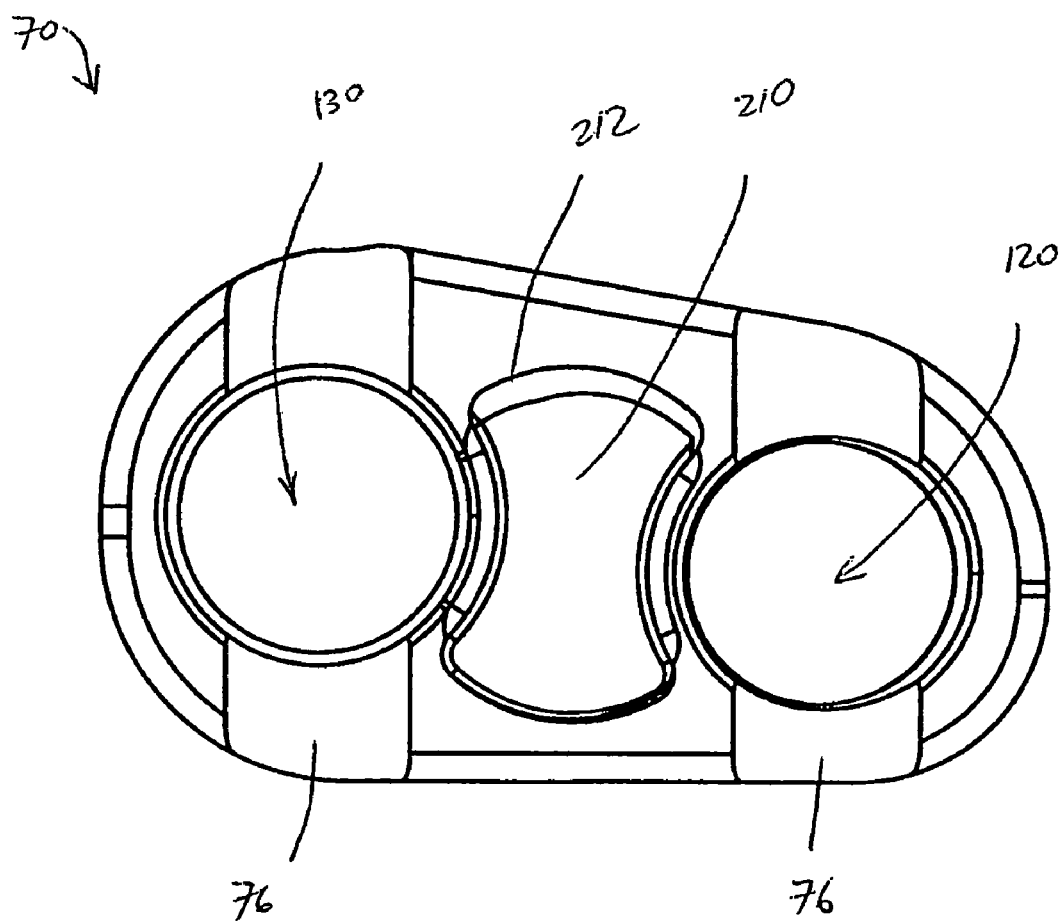
FIG. 23 is a top view of a bottom plate according to a second embodiment of the present invention.
Figure 24:
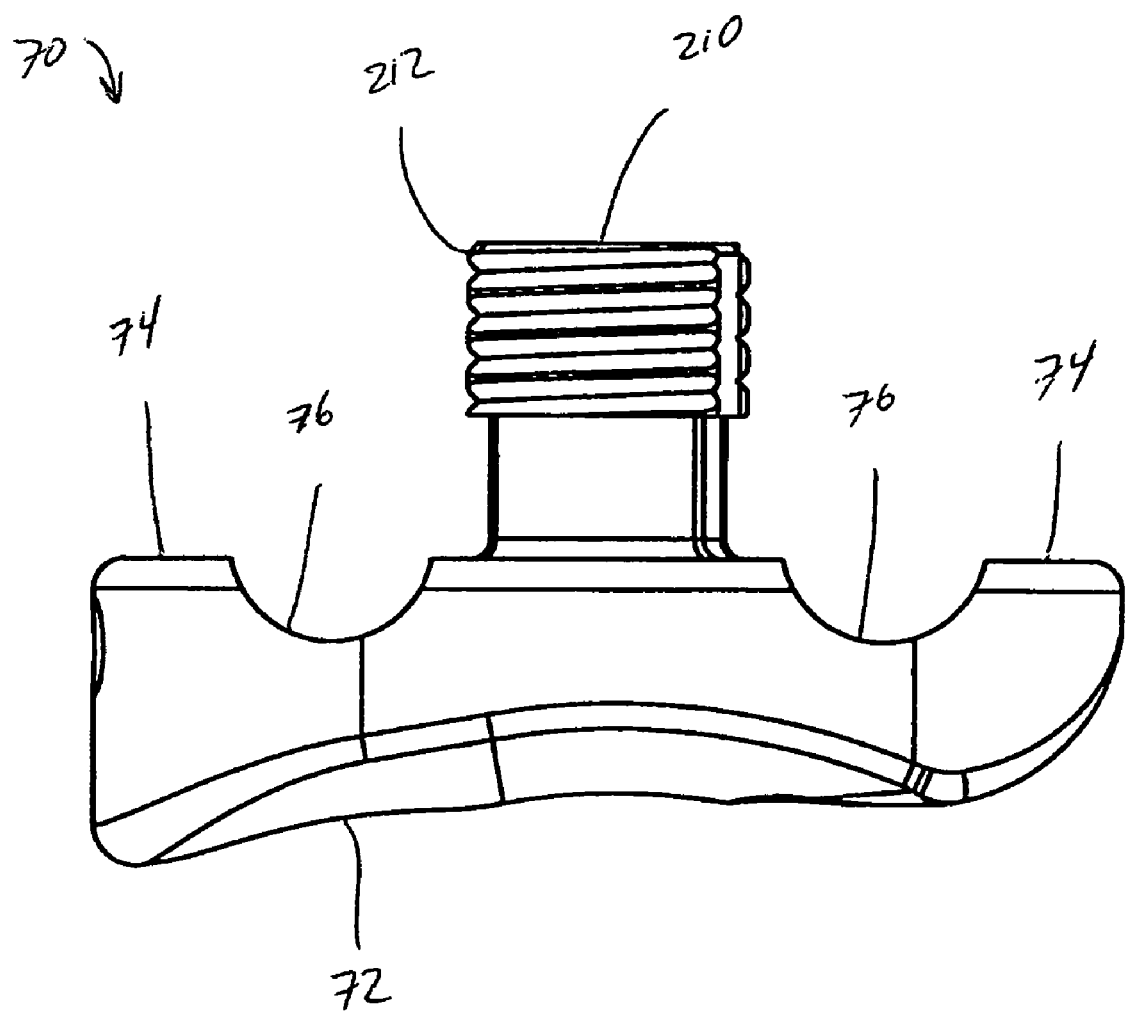
FIG. 24 is a front view of a bottom plate according to a second embodiment of the present invention.
Figure 25:
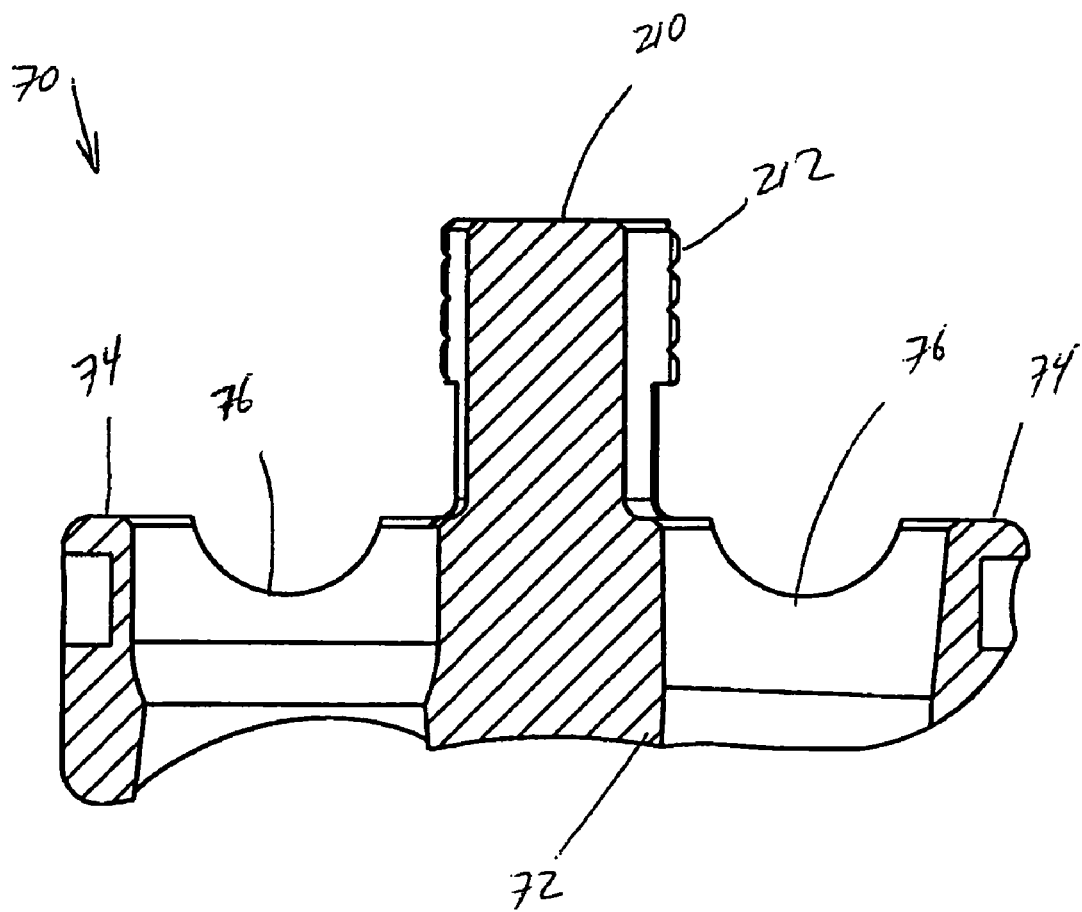
FIG. 25 is a cross-sectional front view of a bottom plate according to a second embodiment of the present invention.
Figure 26:
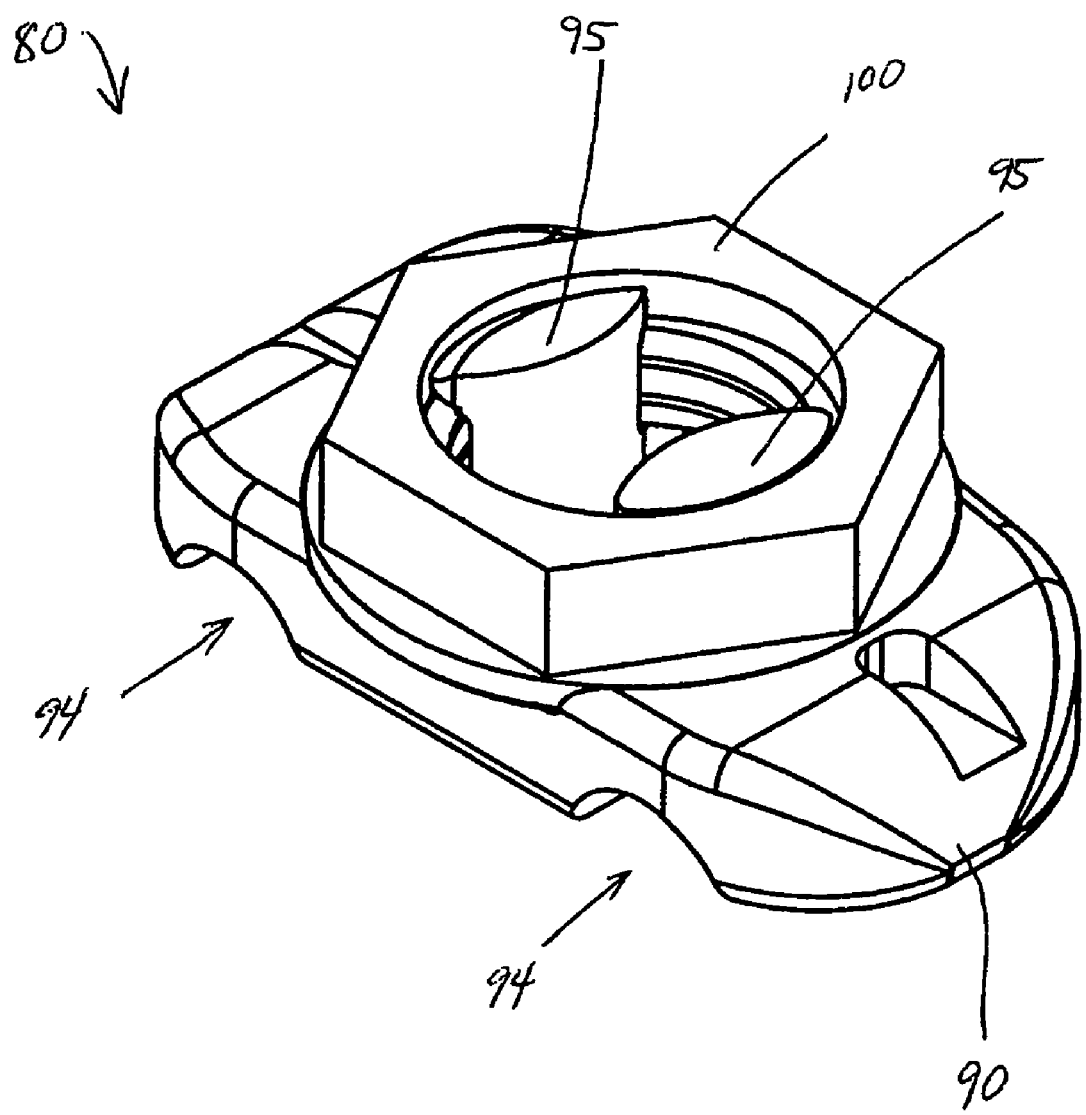
FIG. 26 is a perspective view of a top plate assembly according to a second embodiment of the present invention.
Figure 27:
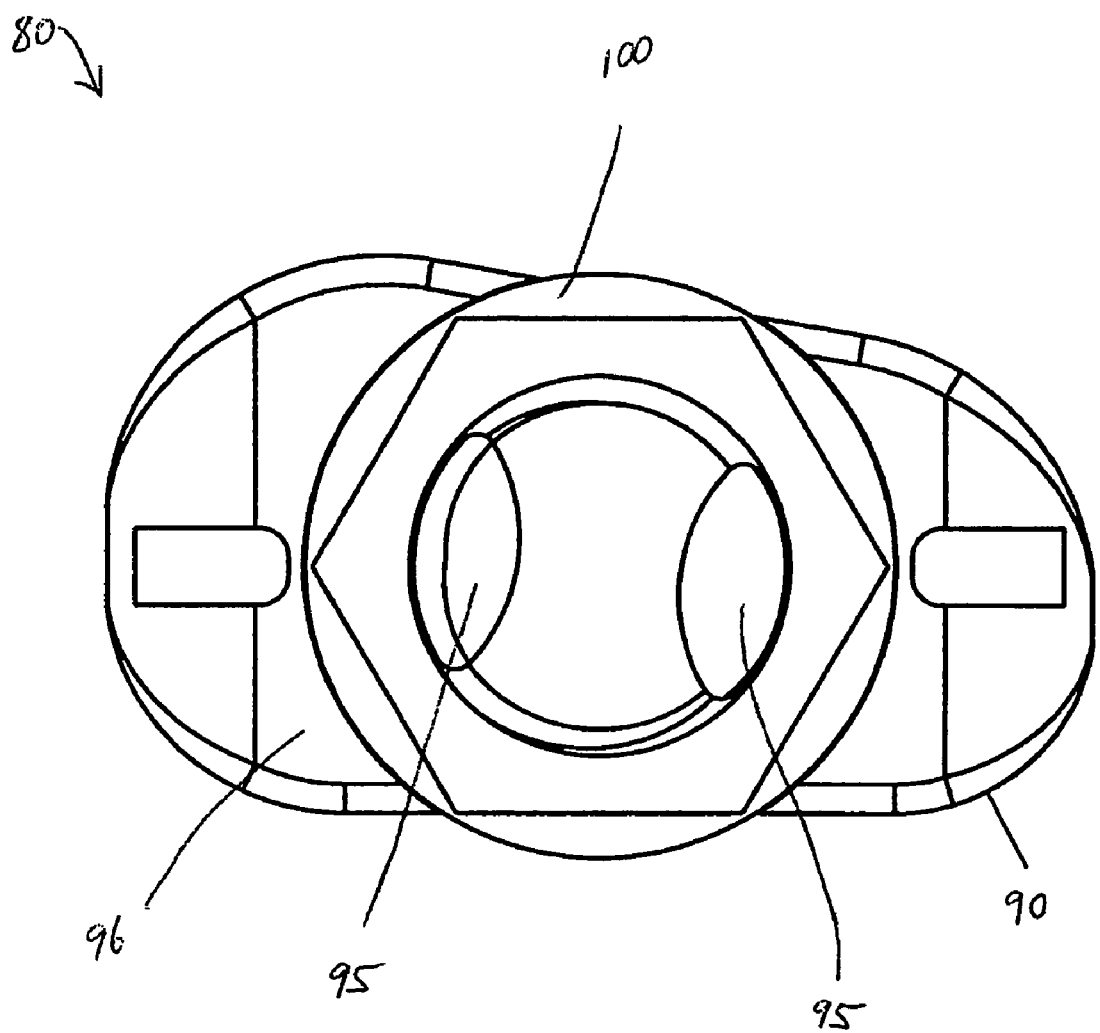
FIG. 27 is a top view of a top plate assembly according to a second embodiment of the present invention.
Figure 28:
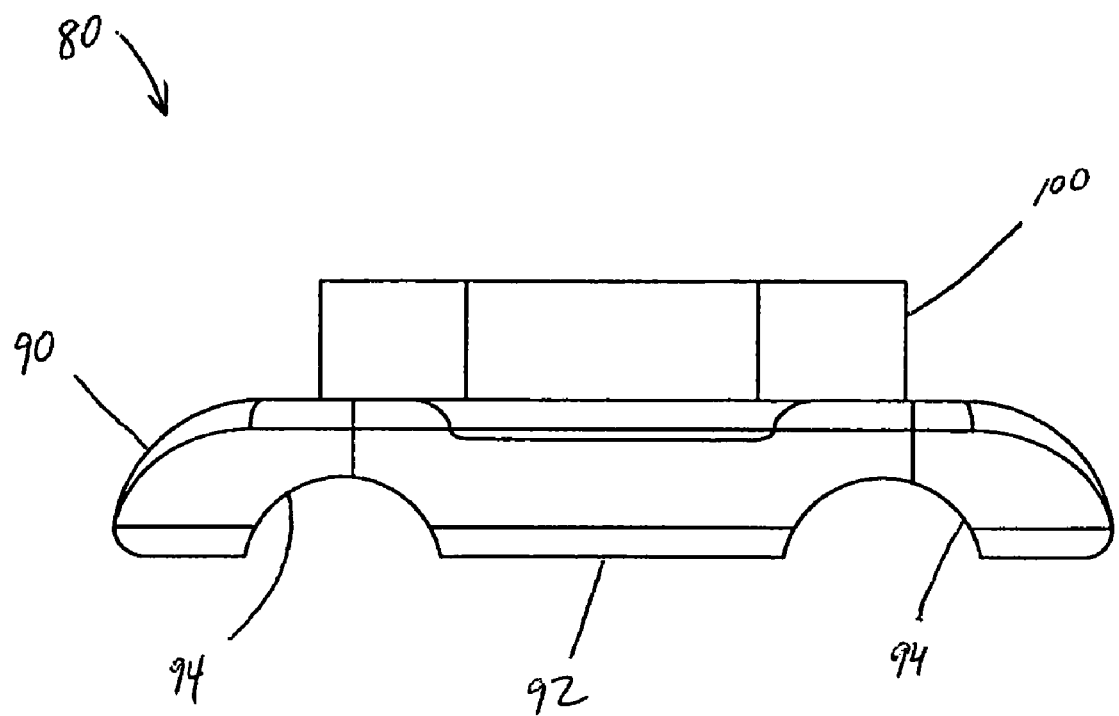
FIG. 28 is a front view of a top plate assembly according to a second embodiment of the present invention.
Figure 29:
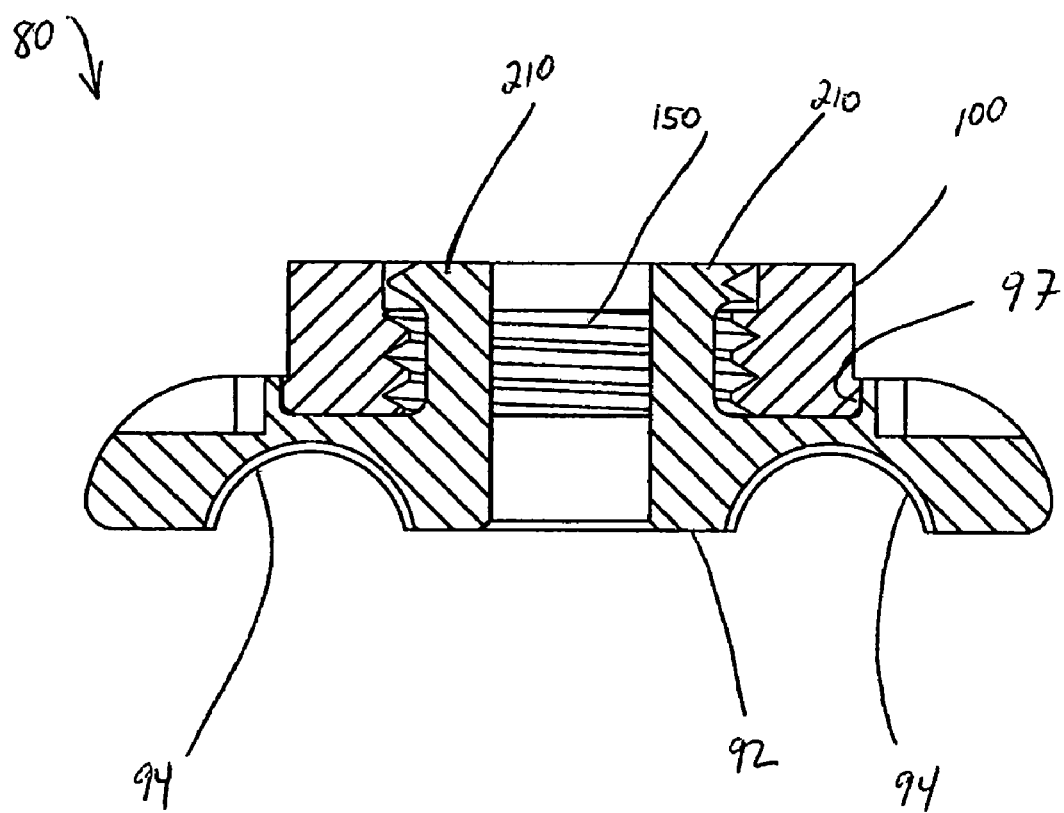
FIG. 29 is a cross-sectional front view of a top plate assembly according to a second embodiment of the present invention.
Figure 30:
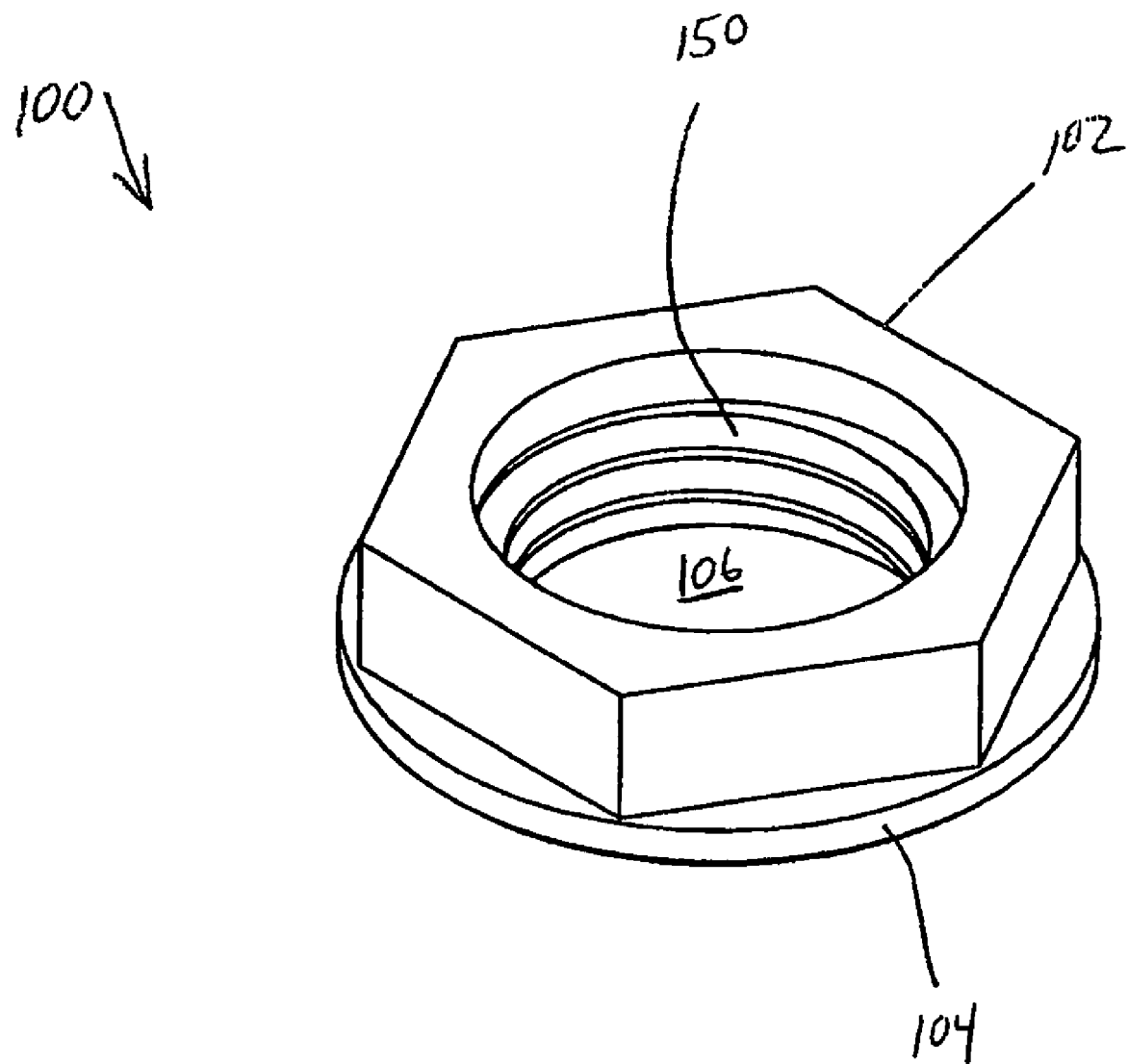
FIG. 30 is a perspective view of a cap according to a second embodiment of the present invention.
Figure 31:
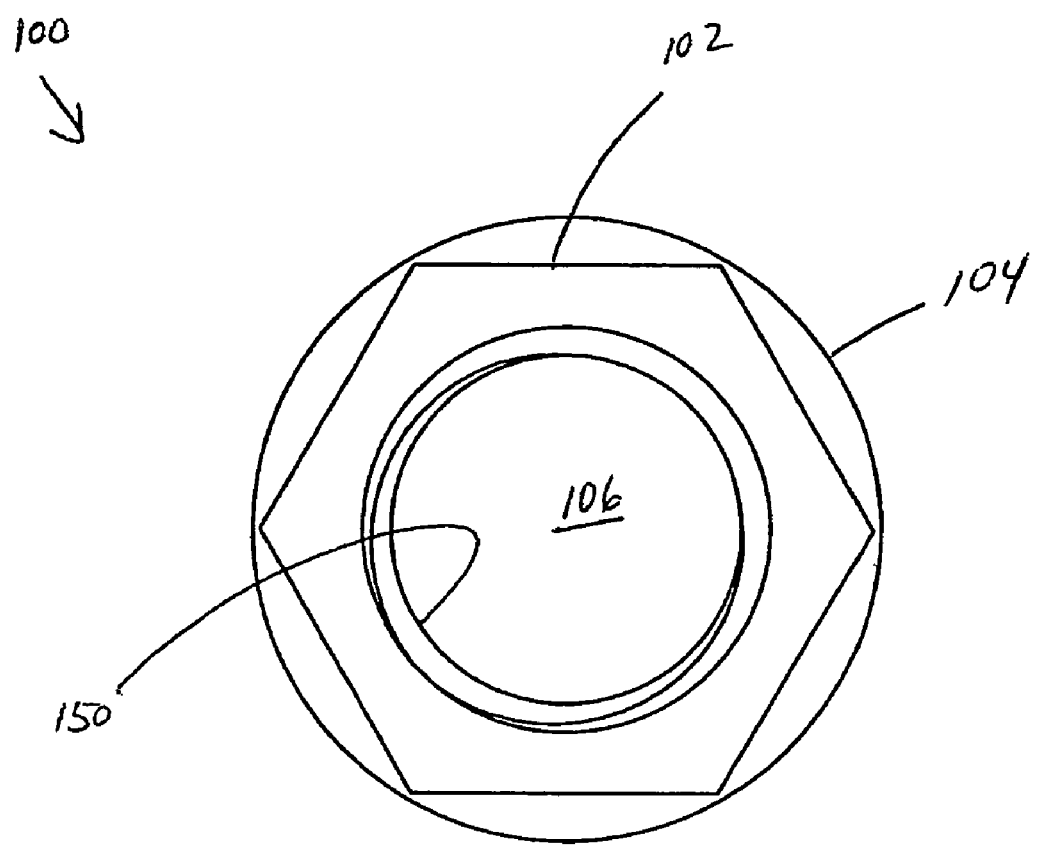
FIG. 31 is a top view of a cap according to a second embodiment of the present invention.
Figure 32:
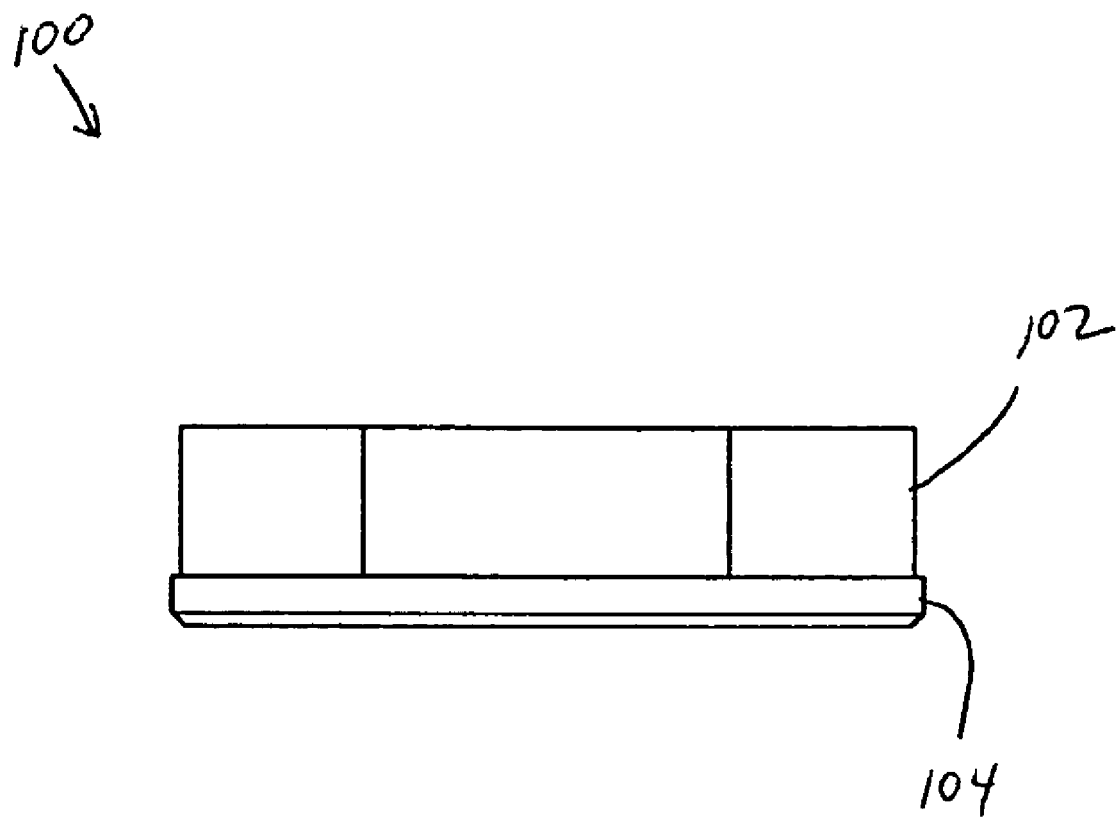
FIG. 32 is a front view of a cap according to a second embodiment of the present invention.
Figure 33:
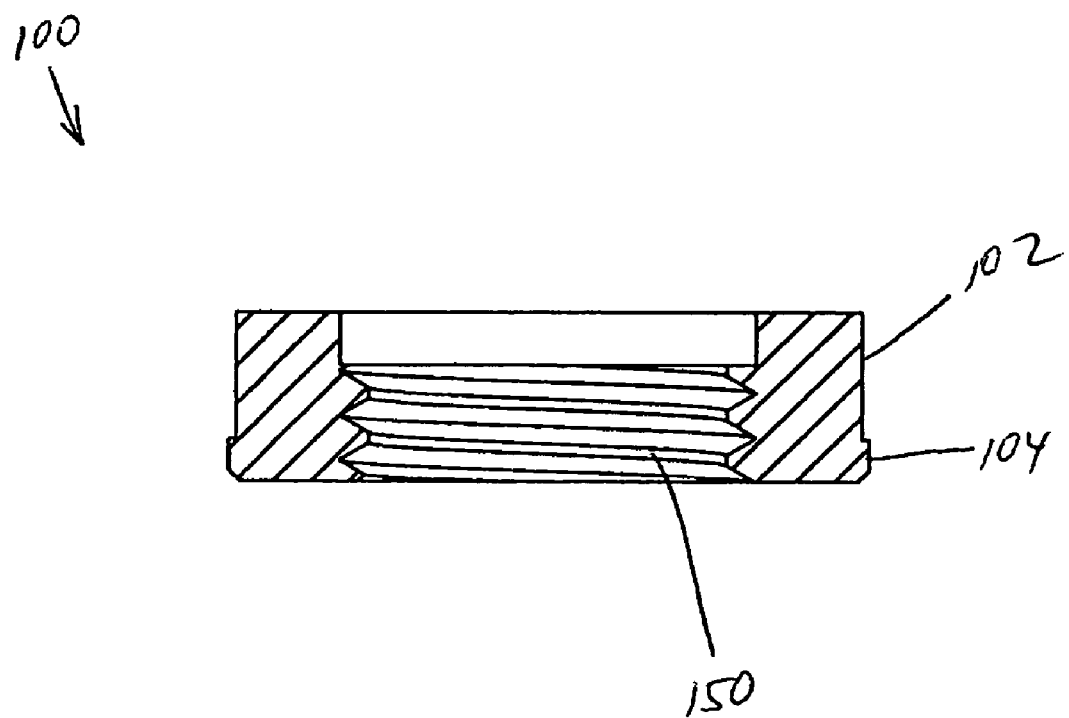
FIG. 33 is a cross-sectional detail view of the threads of the cap shown in FIG. 30.
Figure 34:
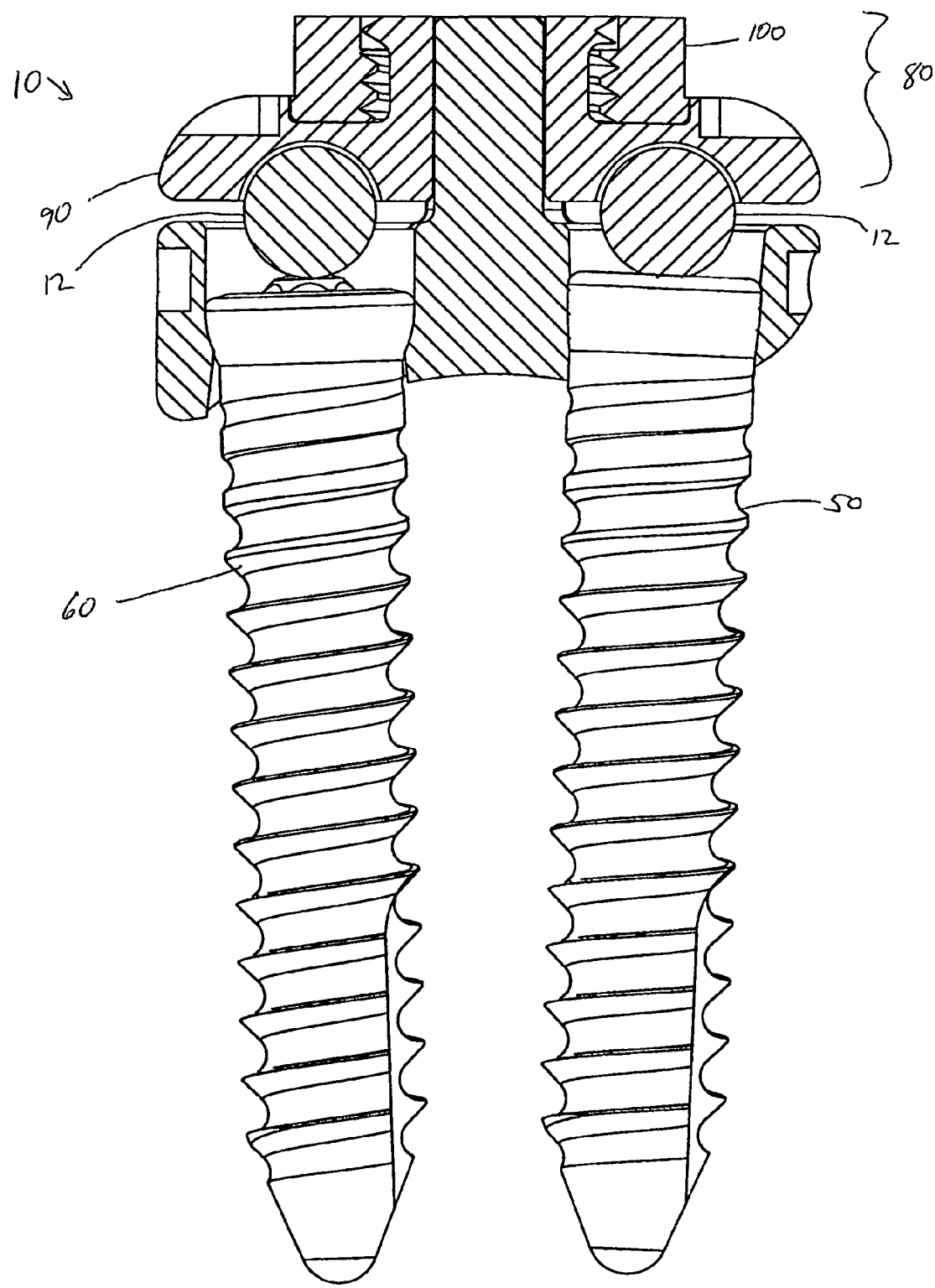
FIG. 34 is a cross-sectional front view of a second embodiment of the present invention shown with one monoaxial screw and one polyaxial screw in use.

Referring now to FIGS. 17 and 18, an exemplary polyaxial screw 60 is shown. It should be noted, however, that the invention is usable with various types of fasteners and the description herein of only two exemplary embodiments is not intended to limit the invention in any way. The polyaxial screw 60 has a partially spherical head 62 shown with a hexagonal recess 64 allowing it to be driven with a standard allen type wrench. It should be noted that many types of driving mechanisms, and therefore recesses 64, are possible. The spherical head 62 mates with the spherical undercut 132 in the second hole 130 in the bottom plate 70 to create a kind of ball and socket connection. The polyaxial screw 60 may be driven at one of many angles, ranging preferably from 0 to approximately 30 degrees, relative to the centerline of the hole 130 while still seating firmly in the bottom plate 70. The spherical undercut 132 is preferably located such that, after the polyaxial screw 60 is driven into the bone, the highest point of the head 62 will be level with, or perhaps slightly above, the lowest point in the recess 76. Therefore, when the cap 100 is rotated to engage the cam projection 110, the rod 12 compresses the head 62 and locks in the angle of the polyaxial screw 60 relative to the bottom plate 70. This relation is shown in detail in FIG. 19.

Referring again to FIGS. 1 and 2, cross connectors 40 located between the mounting constructs 20, 30 are also optionally provided. Two cross connectors are shown in the figures, but obviously any number (or none at all) of cross connectors may be used depending on the distance between the mounting constructs 20, 30 and the amount of additional torsional stability required. A cross connector 40 is preferably substantially identical to a mounting construct except the bottom plate 70 of the cross connector does not contain screw holes 120 and 130.

In the preferred embodiment, the invention is formed of a material suitable for implantation in the human body, still more preferably a metal, with sufficient rigidity for the particular load to be applied. In this embodiment, the taper lock screws 50 have a diameter of approximately 7.0 mm, the polyaxial screws 60 have a diameter of approximately 7.0 mm, and the surgical rods 12 have a diameter of approximately 5.0 mm. One or more cross connectors may additionally be used as required for torsional stability.

FIGS. 20-34 depict a second, threaded embodiment of the invention. Many features and structures of this embodiment are similar to that of the first, cam embodiment described above and have been labeled accordingly. These similar features function in generally the same manner, so only the differences will be discussed below.

FIGS. 22-25 show the bottom plate 70 of the second embodiment. In this embodiment, a threaded projection 210 is disposed atop the upper surface 74. Threads 212 are disposed on the threaded projection 210 to threadingly engage the cap 100 when the bottom plate 70 and the top plate assembly 80 are mated.

Referring now to FIGS. 26-29, the top plate assembly 80 comprises a top plate 90 and a cap 100. The top plate 90 of the second embodiment typically does not (although it is possible to have) comprise one or more projections 99 to engage grooves 105. Referring to FIGS. 30-34, the cap 100 of this embodiment comprises threads 150 to engage the threaded projection 210 to lock the construct together.

While there has been described and illustrated various features and particular embodiments of a novel thoracolumbar fixation system, it will be apparent to those skilled in the art that variations and modifications may be possible without deviating from the broad spirit and principle of the present invention, which shall be limited solely by the scope of the claims appended hereto.

What is claimed is:

1. A mounting construct for a bone fixation rod system comprising:

a bottom plate having a lower surface for engaging a vertebral body and an upper surface having at least one recess therein for accommodating a bottom surface of a rod, said bottom plate further comprising at least one hole through said lower surface and said upper surface for receiving a bone fixation anchor, and a first projection having a proximal end connected to said upper surface of said bottom plate and a distal end extending outwardly therefrom having a first non-threaded engagement structure thereon;

a top plate having an upper surface and a lower surface having at least one recess therein for accommodating an upper surface of said rod, said top plate further comprising an opening through said upper surface and said lower surface for receiving said first projection;

a cap rotatable from an unlocked position to a locked position having an opening therethrough and having a second non-threaded engagement structure disposed about said opening for releasably lockably coupling with said first non-threaded engagement structure of said bottom plate to secure said top plate to said bottom plate; and at least one bone fixation anchor for securing said mounting construct to a bone through said at least one hole;

wherein said first non-threaded engagement structure further comprises at least one cam surface disposed about an outer surface of said first projection; and wherein said top plate further comprises two projections depending upwardly from said upper surface for receiving said first projection therebetween.

2. The mounting construct of claim 1 wherein said second non-threaded engagement structure further comprises at least one cam surface that rotatably engages said at least one cam surface of said first non-threaded engagement structure to secure said top plate to said bottom plate.

3. The mounting construct of claim 2 wherein said at least one bone fixation anchor comprises a fixed bone screw.

4. The mounting construct of claim 3 wherein said fixed bone screw is received within said at least one hole for fixing said mounting construct to a bone.

5. The mounting construct of claim 4, further comprising at least one rod, wherein said rod is received in said at least one recess and a lower surface of said rod prevents said fixed bone screw from backing out of said hole.

6. The mounting construct of claim 5 wherein said top plate further comprises a cap recess therein surrounding said opening for receiving a bottom surface of said cap when said cap is installed in said mounting construct.

7. The mounting construct of claim 6 wherein said cap recess further comprises at least one detent or protrusion that engages a mating structure on said cap to provide a tactile feedback to a user.

8. The mounting construct of claim 2 wherein said at least one bone fixation anchor comprises a polyaxial bone screw having a head with an upper surface.

9. The mounting construct of claim 8, further comprising at least one rod, wherein said rod is received in said at least one recess and a lower surface of said rod contacts said upper surface of said head of said polyaxial bone screw when said cap is rotated to said locked position, thus locking said polyaxial screw position.

10. A mounting construct for a bone fixation rod system comprising:
   a bottom plate having a lower surface for engaging a vertebral body and an upper surface having at least one recess therein for accommodating a bottom surface of a rod, said bottom plate further comprising at least one hole through said lower surface and said upper surface for receiving a bone fixation anchor, and a first projection having a proximal end connected to said upper surface of said bottom plate and a distal end extending outwardly therefrom having a first engagement structure comprising male threads disposed on an outer surface of said projection;
   a top plate having an upper surface and a lower surface having at least one recess therein for accommodating an upper surface of said rod, said top plate further comprising an opening through said upper surface and said lower surface for receiving said first projection;
   a cap rotatable from an unlocked position to a locked position having an opening therethrough and having a second engagement structure disposed about said opening for releasably lockably coupling with said first engagement structure of said bottom plate to secure said top plate to said bottom plate; and
   at least one bone fixation anchor for securing said mounting construct to a bone through said at least one hole, wherein said top plate further comprises two projections depending upwardly from said upper surface for receiving said first projection therebetween.

11. The mounting construct of claim 10 wherein said second engagement structure further comprises female threads that rotatably engage said male threads of said first engagement structure to secure said top plate to said bottom plate.

12. The mounting construct of claim 11 wherein said at least one bone fixation anchor comprises a fixed bone screw.

13. The mounting construct of claim 12 wherein said fixed bone screw is received within said at least one hole for fixing said mounting construct to a bone.

14. The mounting construct of claim 13, further comprising a rod wherein said rod is received in said at least one recess and a lower surface of said rod prevents said fixed bone screw from backing out of said hole.

15. The mounting construct of claim 11 wherein said at least one bone fixation anchor comprises a polyaxial bone screw having a head with an upper surface.

16. The mounting construct of claim 15, further comprising a rod wherein said rod is received in said at least one recess and a lower surface of said rod contacts said upper surface of said head of said polyaxial bone screw when said cap is rotated to said locked position, thus locking said polyaxial screw position.

* * * * *